US010499839B1

(12) United States Patent
Acosta et al.

(10) Patent No.: US 10,499,839 B1
(45) Date of Patent: *Dec. 10, 2019

(54) OPTIMIZED BIOPHOTONIC SENSORS

(71) Applicant: Verily Life Sciences LLC, Mountain View, CA (US)

(72) Inventors: Victor Marcel Acosta, San Francisco, CA (US); Bo Zeng, Berkeley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/687,932

(22) Filed: Aug. 28, 2017

Related U.S. Application Data

(63) Continuation of application No. 14/484,164, filed on Sep. 11, 2014, now Pat. No. 9,763,607.

(51) Int. Cl.
*A61B 5/1455* (2006.01)
*A61B 5/00* (2006.01)
(Continued)

(52) U.S. Cl.
CPC ........ *A61B 5/14556* (2013.01); *A61B 5/0022* (2013.01); *A61B 5/1495* (2013.01);
(Continued)

(58) Field of Classification Search
None
See application file for complete search history.

(56) References Cited

U.S. PATENT DOCUMENTS 7,225,005 B2   5/2007 Kaufman et al.
9,763,607 B1   9/2017 Acosta et al.
(Continued)

FOREIGN PATENT DOCUMENTS

WO   2011072401 A1   6/2011

OTHER PUBLICATIONS

Wang et al., "MCML—Monte Carlo modeling of light transport in multi-layered tissues", Computer Methods and Programs in Biomedicine, 47 (1995) 132-146.
Wang et al., "CONV—convolution for response to a finite diameter photon beam incident on multi-layered tissues," Computer Methods and Programs in Biomedicine, 54 (1997) 141-150.
(Continued)

*Primary Examiner* — Eric F Winakur
*Assistant Examiner* — Marjan Fardanesh
(74) *Attorney, Agent, or Firm* — McDonnell Boehnen Hulbert & Berghoff LLP

(57) ABSTRACT

Methods and devices are provided for optically interrogating subsurface tissues of a body. Optical interrogation includes illumination of a target tissue through an external body surface and detection of light emitted in response to the illumination. Parameters of such optical interrogation are controlled according to operational modes that are selected to maximize detector sensitivity to a target property of the target subsurface tissues. Operational modes are selected based on detected properties of the target tissue and of intervening tissues (e.g., thickness of intervening tissues between the target tissue and an external body surface) between the target tissue and an interrogating optical device. Operational modes can be determined based on simulated optical interrogation of subsurface tissue across a range of optical detector configurations and tissue conditions. Operational modes can include calibration curves specifying optical interrogation parameters based on intervening tissue properties.

20 Claims, 9 Drawing Sheets

(51) Int. Cl.
*A61B 5/145* (2006.01)
*A61B 5/1495* (2006.01)

(52) U.S. Cl.
CPC .......... *A61B 5/14546* (2013.01); *A61B 5/681* (2013.01); *A61B 5/748* (2013.01)

(56) References Cited

U.S. PATENT DOCUMENTS

2009/0118622 A1    5/2009   Durkin et al.
2009/0287076 A1   11/2009   Boyden et al.
2010/0030480 A1    2/2010   Wolfgang

OTHER PUBLICATIONS

Jacques, Steven L., "Symposium-in-Print—Light Distributions from Point, Line and Plane Sources for Photochemical Reactions and Fluorescence in Turbid Biological Tissues," Photochemistry and Photobiology, 1998, 67(1) 23-32.
Prahl et al., "A Monte Carlo Model of Light Propagation in Tissue," SPIE Institute Series, vol. 1S 5 (1989) 102-111.

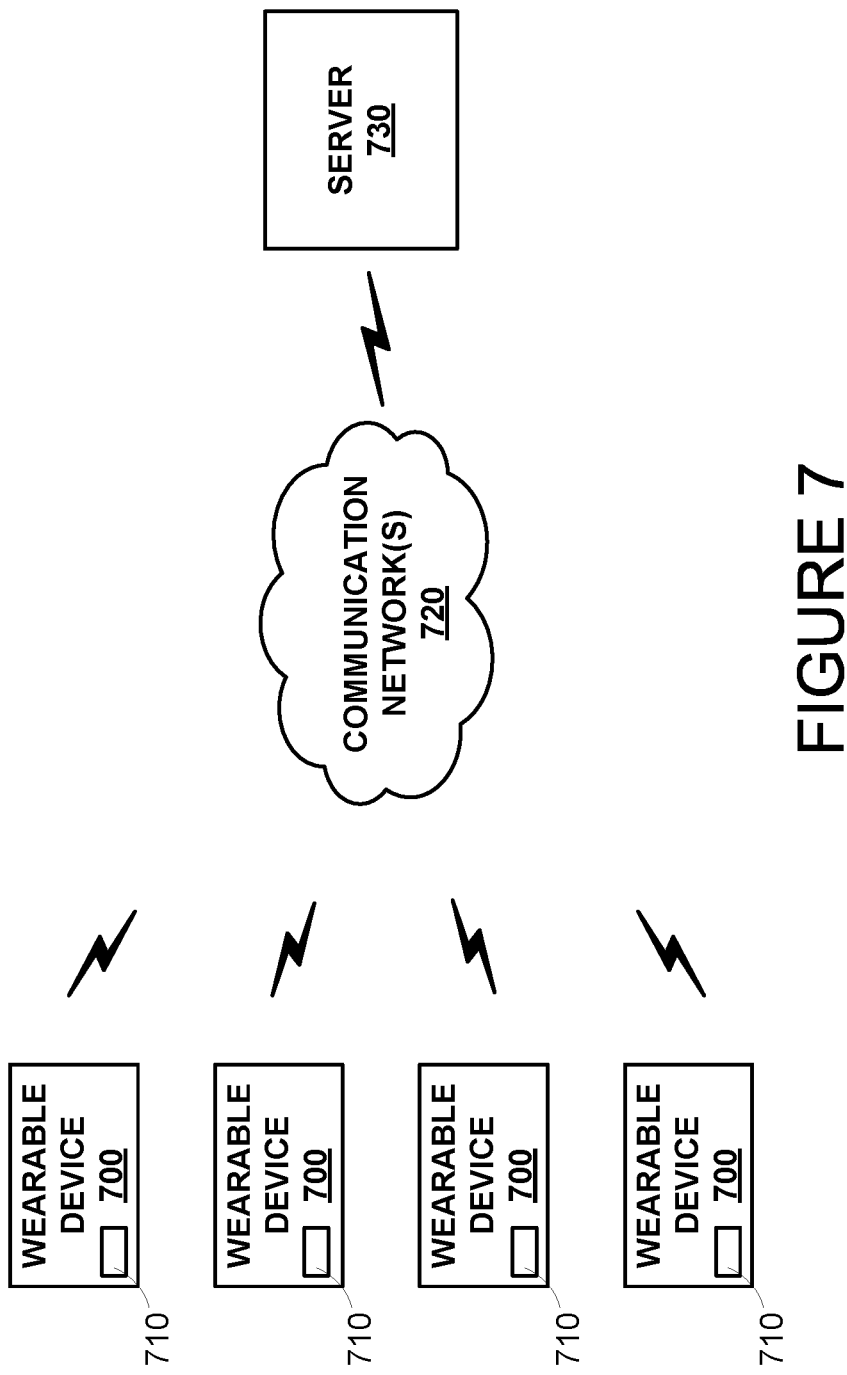

OPTIMIZED BIOPHOTONIC SENSORS

CROSS-REFERENCE TO RELATED APPLICATION

This application is a continuation of U.S. patent application Ser. No. 14/484,164, filed Sep. 11, 2014, which is incorporated herein by reference.

BACKGROUND

Unless otherwise indicated herein, the materials described in this section are not prior art to the claims in this application and are not admitted to be prior art by inclusion in this section A number of scientific methods have been developed in the medical field to examine physiological conditions of a person, for example, by detecting and/or measuring one or more analytes in a person's body or other environment. The one or more analytes could be any analytes that, when present in or absent from the body, or present at a particular concentration or range of concentrations, may be indicative of a medical condition or health of the person. The one or more analytes could include dissolved gases, body fluids, enzymes, hormones, proteins, cells or other molecules.

Detecting and/or measuring one or more analytes in a person's body or other environment can be accomplished non-invasively. That is, light, sound, electromagnetic waves, or other interrogating energies can be emitted into an environment of interest, and the interaction of elements of the environment of interest with the emitted interrogating energies (e.g., interaction through absorption, reflection, refraction, scattering, fluorescence, transduction, or some other process or combination of processes) can be detected (e.g., by receiving some light, sound, electromagnetic wave, or other energy emitted from the environment of interest in response to the interrogating energy) and used to determine one or more properties of the environment of interest. In some examples, this could include emitting interrogating energies that interact with one or more contrast agents introduced into the environment of interest, e.g., fluorophores configured to selectively interact with a specific analyte in the environment of interest.

SUMMARY

Some embodiments of the present disclosure provide a method including: (i) detecting a property of an intervening tissue between an external body surface and a target tissue; (ii) selecting an operational mode of an optical device based on the detected property of the intervening tissue, wherein the optical device is configured to illuminate the target tissue through the external body surface and the intervening tissue and to detect light emitted from the target tissue through the intervening tissue and the external body surface in response to the illumination, wherein selecting the operational mode of the optical device comprises selecting the operational mode to maximize a sensitivity of the optical device to a target property of the target tissue; and (iii) operating the optical device in the selected operational mode to detect the target property of the target tissue, wherein operating the optical device to detect the target property of the target tissue comprises emitting light through the external body surface and the intervening tissue to illuminate the target tissue according to the selected operational mode and detecting light emitted from the target tissue through the intervening tissue and the external body surface in response to the illumination according to the selected operational mode.

Some embodiments of the present disclosure provide a system including: (i) means for detecting a property of an intervening tissue between an external body surface and a target tissue; (ii) means for selecting an operational mode of an optical device based on the detected property of the intervening tissue, wherein the optical device includes means for illuminating the target tissue through the external body surface and the intervening tissue and means for detecting light emitted from the target tissue through the intervening tissue and the external body surface in response to the illumination, wherein selecting the operational mode of the optical device comprises selecting the operational mode to maximize a sensitivity of the optical device to a target property of the target tissue; and (iii) means for operating the optical device in the selected operational mode to detect the target property of the target tissue, wherein operating the optical device to detect the target property of the target tissue comprises emitting light through the external body surface and the intervening tissue to illuminate the target tissue according to the selected operational mode and detecting light emitted from the target tissue through the intervening tissue and the external body surface in response to the illumination according to the selected operational mode.

Some embodiments of the present disclosure provide a device including: (i) a light source, wherein the light source is configured to illuminate a target tissue through an external body surface and an intervening tissue between the external body surface and the target tissue; (ii) a light sensor, wherein the light sensor is configured to detect light emitted from the target tissue through the intervening tissue and the external body surface in response to illumination by the light source; and (iii) a controller, wherein the controller is configured to: (a) detect a property of the intervening tissue; (b) select an operational mode of the device based on the detected property of the intervening tissue, wherein selecting the operational mode of the device comprises selecting the operational mode to maximize a sensitivity of the device to a target property of the target tissue; and (c) operate the device in the selected operational mode to detect the target property of the target tissue, wherein operating the device to detect the target property of the target tissue comprises operating the light source to emit light through the external body surface and the intervening tissue to illuminate the target tissue according to the selected operational mode and operating the light sensor to detect light emitted from the target tissue through the intervening tissue and the external body surface in response to the illumination according to the selected operational mode These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7 is a block diagram of an example system that includes a plurality of wearable devices in communication with a server.

DETAILED DESCRIPTION

Figure 1:
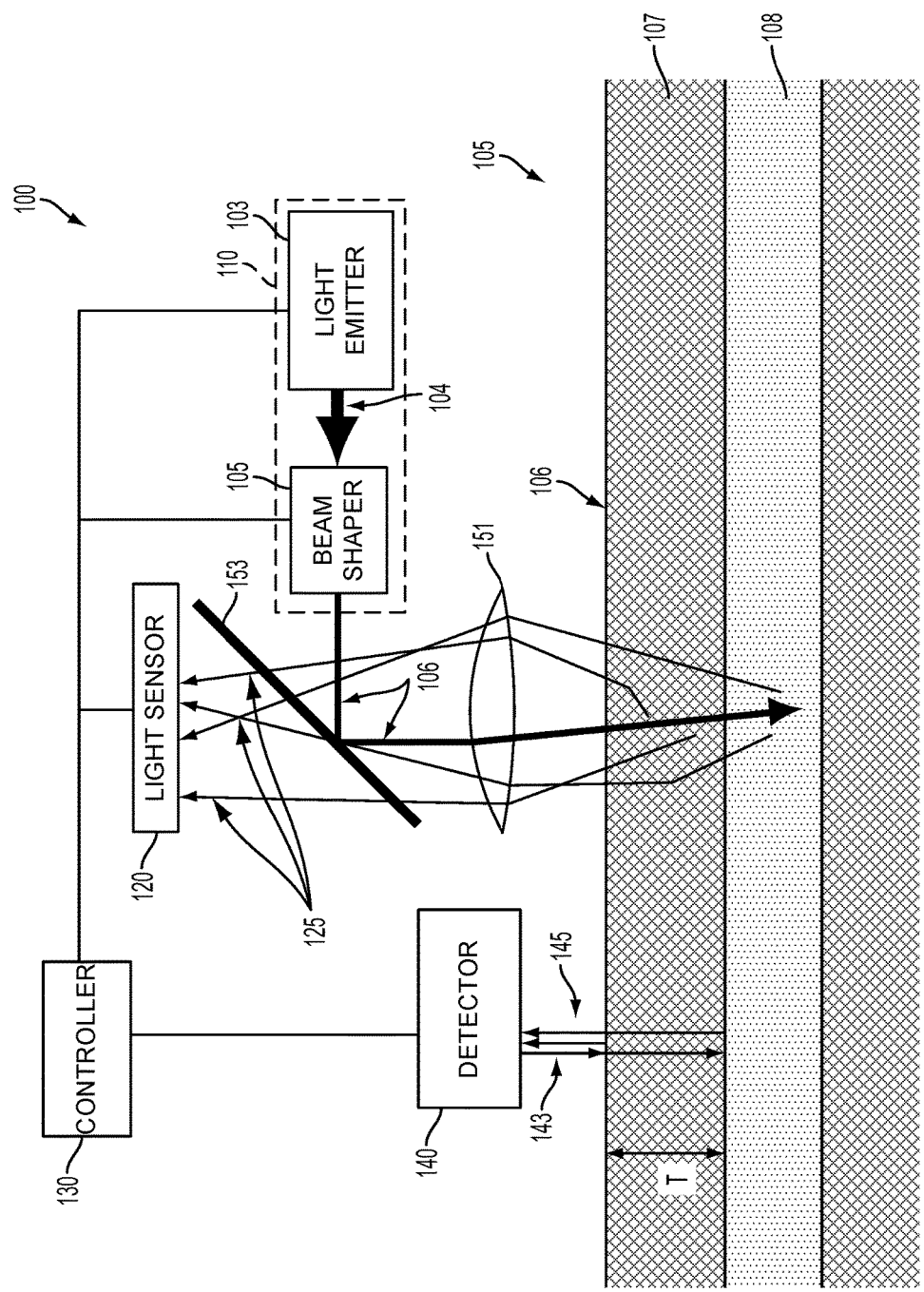
FIG. 1 is side partial cross-sectional view of a device, while positioned proximate to a target tissue that is beneath an external body surface.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of properties of a tissue, element of an environment, and/or analyte is desired. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vitro applications are possible as well. Accordingly, the environment may also include a test tube or other vessel for holding a fluid.

I. Overview

The operation of an optical device (e.g., an apparatus configured to detect a property of an environment by emitting illumination toward the environment and detecting light received from the environment in response to the illumination) to detect a property of a target tissue in a biological environment (e.g., a portion of subsurface vasculature in a body) can be sensitive to one or more properties of the target tissue or other tissues or elements of the biological environment. That is, the sensitivity of the optical device to a property of interest (e.g., an oxygen saturation of blood in a portion of subsurface vasculature, a property (e.g., location, presence, concentration) of fluorophores in the target tissue) could be related to other properties of the biological environment (e.g., a scattering property of an intervening tissue between the target environment and the optical device, a depth of the target tissue beneath an external body surface within a scattering intervening tissue, and/or a scattering property of the target tissue). The sensitivity could further be related to properties of the operation of the optical device (e.g., an intensity of illumination emitted by the optical device, a width of a beam of illumination emitted by the optical device, a field of view of a photodetector, a focal length of an optical assembly of the optical device) in a way that is dependent on the other properties of the biological environment. That is, the sensitivity of the optical device to the property of interest could be maximized when a property of the biological environment is a first value by operating the optical device according to a first operational mode (e.g., a first beam width, a detector field of view, or some other detector property or combination of properties) and the sensitivity of the optical device to the property of interest could be maximized when the property of the biological environment is a second value by operating the optical device according to a second operational mode.

Other properties of the biological environment could include properties of the geometry, composition, or other properties of the biological environment and/or of the location of the optical device relative to the biological environment and/or elements thereof. For example, the other properties could include scattering coefficients of one or more intervening layers of tissue between an external body surface and a target tissue in a biological environment and respective thicknesses and geometries of those layers. The other properties could include a depth of a target tissue within the biological environment from an external surface or boundary of the biological environment at which the optical device is disposed (e.g., the depth of a portion of subsurface vasculature beneath an external body surface). The other properties could change over time, and/or could depend on the location of the optical device relative to the biological environment that could also change over time. Thus, the other properties could be detected repeatedly over time (e.g., at a specified sample rate) and the operation of the optical device to detect a property of interest could be responsively updated according to operational modes corresponding to the repeatedly detected other properties.

Operational modes corresponding to maximum-sensitivity operation of the optical device to detect a property of interest given a detected other property of the biological environment could be determined by a variety of methods. Maximally-sensitive operational modes could be determined through empirical experimentation, varying various parameters of a physical model of an environment of interest (e.g., a biological environment containing a portion of subsurface vasculature and intervening tissues between the portion of subsurface vasculature and an external body surface) and the optical device and determining corresponding optical device sensitivities when operated to detect the property of interest. Additionally or alternatively, computational models of the environment (e.g., models of light scattering and absorption in multi-layered scattering biological media) and the optical device (e.g., models of light emission, propagation, refraction, diffraction, and reception in relation to simulated components of the optical device) could be used to determine sensitivity of the optical device to the property of interest when operated in various ways to interrogate environments having different configurations (e.g., different scattering coefficients, different depths of subsurface vasculature in biological tissue).

Operational modes of the optical device (e.g., modes defining the width of a beam of illumination, the location, shape, and/or size of a field of view of a photodetector) could be determined, based on the output of the computational model, corresponding to detected other properties of the biological environment (e.g., depth of a portion of subsurface vasculature beneath an external body surface) such that operation of the optical device according to a selected operational mode, responsive to the detection of a corresponding level of the other property of the biological environment, could allow for maximum-sensitivity detection of the property of interest of the target tissue relative to other operations of the optical device. For example, the operational modes could take the form of a calibration curve relating a detected depth of subsurface vasculature to a width of a beam of illumination that could be emitted by the optical device to detect an oxygen saturation of blood in the portion of subsurface vasculature with maximum sensitivity.

Operational modes could be curves (e.g., calibration curves) relating a single detected other property of the biological environment to one or more parameters of operation of the optical device (e.g., a width of a beam of illumination emitted by the optical device, focal length of optics used to image the light received from the target tissue in response to illumination). Additionally or alternatively, the operational modes could be two- or more-dimensional surfaces or functions relating two or more detected other properties of the environment to one or more parameters of operation of the optical device. The operational modes could include other functions, look-up tables, or other algorithms for determining one or more parameters of operation of the optical device. Further, the operational modes could define waveforms, timing diagrams, wavefronts, or other information describing the illumination emitted by the optical device.

Determination of the operational modes by performing a plurality of simulations could be computationally intensive. The operational modes (e.g., calibration curves) corresponding to various detected values of an other property of the environment of the optical device could be determined once and the determined operational modes could be used subsequently to operate one or more optical devices. For example, an optical device could be configured to detect one or more properties of interest of a target tissue of a body. The optical device could be disposed in a wearable device or other portable apparatus that includes a controller configured to operate the device or other apparatus to detect one or more other properties of the biological environment. The controller could additionally operate the optical device according to the previously determined operational modes corresponding to the detected other property to detect a property of interest of the target tissue. For example, calibration curves or other information about the operational modes could be stored in a memory of the device, and the controller could operate the memory to determine an operational mode based on a detected other property.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Optical Detector

Generally, optical interrogation or detection of one or more properties of a target environment (e.g., of a target biological tissue) includes illuminating the target (e.g., by emission of light by a light source, or by some ambient source of illumination) and detecting one or more properties of light emitted (e.g., reflected, refracted, scattered, fluorescently emitted, or emitted by some other mechanism(s)) by the target tissue in response to the illumination. The one or more properties of the target tissue could be related to the one or more properties of the detected light and/or of the illumination. For example, an extinction coefficient, a reflectivity, an absorbance spectrum, a color, a turbidity, an emission spectrum, or some other property or properties of a target tissue could be related to a physiological property of interest and could be interrogated and/or detected optically (e.g., by an optical device that includes a light sensor, a light source, and/or other optical or other components).

Optical detection (e.g., illumination of and detection of light emitted from) of one or more properties of interest of target biological tissues can be affected by properties of the environment of the tissues. For example, illumination and/or light emitted by the target tissue could be scattered, absorbed, or otherwise affected by tissues neighboring the target tissue and/or intervening between the target tissue and an optical detector. Additionally, light illuminating and/or emitted from target elements of a target tissue (e.g., blood cells in blood, fluorophores of a contrast agent bound to a target cell) could be scattered, absorbed, or otherwise affected by other elements of the target tissue. Correspondingly, the sensitivity of an optical detector can be related to parameters of the target tissue and/or neighboring tissue (e.g., an intervening tissue between the target tissue and an external body surface through which an optical detector is configured to illuminate and receive emitted light from the target tissue). Sensitivity could be defined in a variety of ways, including as the minimum change in a property of interest that can be detected using a particular detector (e.g., an optical detector as described herein) operating in a particular way (e.g., emitting a beam of illumination having a particular beam width, detecting light within a particular field of view) to interrogate a particular environment (e.g., a target environment separated from an optical detector by an intervening tissue between the target environment and an external body surface).

In some examples, an optical detector could be operated relative to one or more properties of the target and/or intervening tissues (e.g., to scattering coefficients, thicknesses, geometries, configurations of vasculature, extinction coefficients, absorption spectra) to maximize the sensitivity of the optical detector to a property of interest of the target tissue. This could include configuring and/or operating the optical detector relative to one or more properties (e.g., a noise level, a spectrum, an absolute or relative amplitude, a DC offset magnitude) of a detected property of interest. Additionally or alternatively, the optical detector could be configured and/or operated relative to one or more other properties of the target tissue and/or neighboring tissues (e.g., a thickness, melanin content, or other property of an intervening tissue, a depth of the target tissue beneath an external body surface) that have a known relationship with the sensitivity of the optical device to the property of interest of the target tissue. Such a known relationship could be determined experimentally (e.g., by the optical device or by some other apparatus) or in simulation (e.g., using one or more models of the target tissue and neighboring tissues to simulate operation of the optical detector) for an individual user (e.g., based on measured or otherwise determined properties of tissues of the individual user) or for a population of users.

FIG. 1 illustrates an example device 100 configured to optically detect one or more properties of a portion of subsurface vasculature (POSV) 108 (i.e., a target tissue) of a user 105, where the portion of subsurface vasculature 108 is separated from an overlying external body surface 106 by an intervening tissue 107 (e.g., skin tissue, connective tissue, fat tissue). The intervening tissue has a thickness T between the external body surface 106 and the portion of subsurface vasculature 108.

The device 100 includes a light source 110 configured to emit a beam of illumination 106 into the POSV 108 through the external body surface 106 and the intervening tissue 107 and a light sensor 120 configured to detect emitted light 125 from the target tissue 108 in response to the illumination. Emitted light 125 may also include light emitted (e.g., reflected, scattered, refracted, fluorescently emitted) from the intervening tissue 107 or from other elements or regions in the environment of the POSV 108. The device 100 additionally includes optics including a lens 151 and a beam splitter 153 configured to refract and partially reflect, respectively, the emitted light 125 and the beam of illumination 106. Collectively, the light source 110, light sensor 120 and optics 151, 153 could be referred to as an optical device.

The device 100 additionally includes a detector 140 configured to detect one or more other properties of the POSV 108, intervening tissue 107 and/or external body surface 106 that could be related to the sensitivity of the optical device to a property of interest of the POSV 108. The device 100 includes a controller 130 configured to operate components of the device 100 (e.g., 110, 120, 140).

A variety of properties of the POSV 108 could be optically detected. An oxygen saturation, a volume of blood, a cell fraction of blood, a position or width of the vasculature, a temperature, the concentration or location of some element(s) (e.g., blood cells, fluorophores of a contrast agent) within the POSV 108, or some other property or properties could be related to an absorbance spectrum, excitation spectrum, an emission spectrum, an autofluorescence, a scattering coefficient, an extinction coefficient, a color, or some other optical property of the POSV 108. For example, the concentration and/or location of fluorophores of a contrast agent (e.g., of a contrast agent configured to selectively interact with an analyte of interest in the blood or in some other tissue of interest) could be detected by illuminating, using the light source 110, the POSV 108 with light having wavelengths corresponding to an excitation wavelength of the fluorophores. Light emitted responsively to the illumination by the fluorophores could be detected by the light sensor 120 (e.g., the light sensor and/or optics could include filters or be otherwise selectively sensitive to light having wavelengths corresponding to an emission wavelength of the fluorophores). In another example, the oxygen saturation of blood (e.g., the percentage of the hemoglobin binding sites in the blood that are occupied by oxygen) could be optically detected by detecting one or more features of an absorption spectrum of the blood (e.g., by detecting the extinction coefficient of the blood at one or more wavelengths by illuminating the blood with two or more lights having wavelengths within two or more respective ranges and detecting light responsively emitted by the blood). Other properties of a target tissue could be optically detected by corresponding additional or alternative methods.

As illustrated in FIG. 1, the detector 140 is configured to detect the thickness T of the intervening tissue 107 (which could be related to the depth of the POSV 108 beneath the external body surface 106) through optical coherence tomography (OCT). That is, the detector 140 emits light 143 toward the tissues (e.g., 107, 108) of the user 150 and detects responsively emitted light 145. The detector 140 is configured to detect the time(s) that light takes from being emitted (e.g., as 143) by the detector 140 to being detected (e.g., as 145) and uses the detected timing information to determine the distance to and/or thickness of various layers of tissue (e.g., 107, 108). Additionally or alternatively, the detector 140 could be configured to determine such distance and/or depth information through acoustic means (e.g., by emitting and/or detecting sound waves toward/from the tissues of the user 105 using one or more ultrasonic or other acoustical transducers).

In some embodiments, the detector 140 could be configured to detect other properties of the intervening tissue 107, the POSV 108 (or some other target tissue), or other aspects of the body of the user 105 by some other means. For example, the detector 140 could include an acoustical transducer, an optical coherence tomography (OCT) sensor, a visible light camera, an infrared camera, a laser, a photodetector, an interferometer, or some other components configured to detect a thickness of the intervening tissue 107, a depth of the POSV 108 beneath the external body surface 106, or some other property of the location, thickness, and/or other properties of various elements and tissues of a user 106. The detector 470 could be configured to detect a temperature, a scattering coefficient, an extinction coefficient, an absorbance spectrum, a water content and/or hydration level, a color, a melanin content, a fat content, or some other property or properties of the intervening tissue 107, the POSV 108, and or some other tissues of a user 105 and/or some other biological environment. Additionally or alternatively, elements of the optical detector (e.g., 110, 120, 151, 153) could be configured and/or operated to detect such properties.

As illustrated in FIG. 1, the light source 110 includes a light emitter 103 and a beam shaper 105 configured to emit the beam of illumination 106 such that the beam of illumination 106 has certain specified properties and illuminates the POSV 108 through the external body surface 106 and the intervening tissue 107. The light emitter 103 emits light 104 having one or more properties that are controlled by the beam shaper 105 to result in the beam of illumination 106 being emitted from the light source 110 through the optics 151, 153 and toward the tissue of the user 105. The light emitter could include a variety of light-emitting elements, including light-emitting diodes (LEDs), lasers, A wavelength, a spectral profile, a beam location and angle relative to the optics (151, 153, 120) and/or elements of the POSV 108, a beam diameter, a beam shape, a beam wavefront, an amplitude, an intensity, a polarization, a coherence, or some other property or properties of the beam of illumination 106 could be specified (e.g., according to an operational mode of the device 100). Further, a pattern in time of such properties of the beam of illumination 106 (e.g., a pattern over time of the intensity of the beam of illumination 106) could be specified (e.g., a waveform, a pulse width, a pulse shape, a pulse frequency). Such properties could be specified by a configuration of the light source 110 (e.g., a composition of the light emitter 103 (e.g., a semiconductor composition), optics of the light emitter 103 (e.g., filters, lenses, diffraction gratings), an aperture width and/or shape of the beam shaper 105)) or a method of operation of elements of the light source 110. For example, an iris of the beam shaper 105 could be operated to control a beam width of the beam of illumination 106. Additionally or alternatively, the beam shaper 105 could include a spatial light modulator (SLM; e.g., a micromirror or liquid crystal array)

that could be operated (e.g., the reflectivity, transmittance, or other property of elements of the micromirror or liquid crystal array could be controlled) such that the beam of illumination 106 had one or more specified properties (e.g., a specified wavefront).

The light sensor 120 could include a variety of components that could be operated in a variety of ways. The light sensor 120 may include CMOS, CCD, photodiode, phototransistor, or other optically sensitive elements or combinations thereof. The light sensor could include one or more filters configured to block specified ranges of wavelengths of light from being received by light-sensitive elements of the light sensor. The light sensor could be configured to sense the polarization of light and/or to only detect light of a specified polarization. For example, the light sensor could include a linear polarization filter such that the light sensor only detects light having a polarization aligned with the orientation of the linear polarization filter. The light sensors could be configured to detect one or more properties of light emitted by a fluorophore, a color center in a nanodiamond, a Raman dye, a chemiluminescent material, a bioluminescent material, or some other light emitting substance. The light sensor could be configured to include multiple light sensitive elements configured to detect respective lights having wavelengths within respective ranges.

A variety of parameters of detection of the emitted light 125 could be specified by configuring elements of the light sensor 120 and/or optics 151, 153 and/or by operating the light sensor 120 and/or optics 151, 153 according to an operational mode. For example, the light sensor 120 and/or optics 151, 153 could be configured and/or operated to specify a field of view (relative to the POSV 108 and/or the beam of illumination 105), a wavelength and/or spectrum of sensitivity, a focal length, a polarization of sensitivity, an exposure level, a contrast, a dynamic range, a temporal bandwidth, or some other parameter(s) of detection of the emitted light 125. For example, the location and/or orientation of the light sensor 120 and/or optics (e.g., 151, 153, additional filters, lenses, mirrors, beam splitter, diffraction gratings, or other elements (not shown)) could be controlled (e.g., by servos, motors, or other actuators) to control a field of view, a focal length, or some other parameter(s) of detection of the emitted light 125.

Additionally or alternatively, the light source 120 (e.g., electronic elements of the light source) could be operated to control one or more parameter(s) of detection of the emitted light 125. For example, a sensitivity to emitted light, a contrast, an exposure level, a dynamic range, or some other property of detection of the emitted light 125 could be specified by controlling an integration time, a bias voltage, a bias current, or some other electronic property of a light-sensitive element(s) (e.g., of a CCD element) of the light sensor 120. In another example, the light sensor 120 could include a multipixel photodetector (e.g., a CCD, an array of photodiodes, active pixel sensors, or other light sensitive elements), and a field of view of the detection of the emitted light 125 could be controlled by detecting the emitted light 125 using a specified set of pixels (i.e., set of individual light sensitive units or areas) of the multipixel photodetector.

The controller 130 can operate the detector 140 to determine a property (e.g., thickness) of the intervening tissue 107. The controller 130 can select an operational mode (e.g., a specified configuration and/or operation of the light source 110, light sensor 120, optics 151, 153, and/or other elements of the device 100) and operate the optical device according to the selected operational mode to detect a property of interest of the POSV 108. Selection of the operational mode is based on the determined property of the intervening tissue 107. The operational mode could specify one or more properties of the configuration or operation of the optical device (e.g., a width of the beam of illumination 106, an intensity of the beam of illumination 106, a field of view of emitted light 125 detected by the light sensor 120, an integration time of a light sensitive element of the light sensor 120). The controller 130 could select the operational mode from a set of operational modes stored on a data storage of the device 100 or could receive the selected operational mode from a remote device (e.g., a server) in communication with the controller 130 after transmitting the determined property of the intervening tissue 107. Additionally or alternatively, the controller 130 could operate the optical device to determine the property of the intervening tissue 107.

The set of operational modes used to select the selected operational mode based on the detected property of the intervening tissue 107 could take a variety of forms. In some examples, the set of operational modes could be described by one or more calibration curves relating a detected property of the intervening tissue to a value of a parameter of the device 100 (e.g., a beam width, a field of view) corresponding to configuration and/or operation of the device 100 such that the device 100 is maximally sensitive to a property of interest of the POSV 108. Additionally or alternatively, the set of operational modes could include a discrete set of operational states where individual operational states (e.g., individual sets of pixels of a multipixel element of the light sensor 120, individual sets of opaque elements of a spatial light modulator of the beam shaper 105) could correspond to values and/or ranges of values of the detected property of the intervening tissue.

Detecting the property of the intervening tissue 107 and/or selecting an operational mode based on the detected property could be performed periodically (e.g., at a specified frequency). Additionally or alternatively, detecting the property of the intervening tissue 107 and/or selecting an operational mode based on the detected property could be performed responsive to some determination, e.g., a determination that a noise level of a property of interest of the POSV 108 detected by operating the optical device is above a specified threshold. Other operations of the device 100 to detect the property of the intervening tissue 107 and/or to select an operational mode are anticipated.

Note that the use of optics 151, 153 in common between the light source 110 and the light sensor 130 is intended as a non-limiting example. The light source 110 and light sensor 120 could be configured to emit beam of illumination 106 and received emitted light 125, respectively, via respective separate optical elements, through common optical elements, or via some combination of in-common and separate optical elements. Further, the device 100 could include servos, motors, or other actuators configured to control the configuration of such optical elements (e.g., to control a focal length, a set of filters applied to a beam path, a location and/or orientation of a mirror in a beam path) according to an application (e.g., according to the specification of an operational mode).

Note that the tissues of the user 105 are intended as a non-limiting example. Tissues could include additional layers of the intervening tissue 107 and/or of the POSV 108 (i.e., of the target tissue) and/or the intervening tissue 107 and/or of the POSV 108 could have more complicated geometries (e.g., curved geometries, branched structures, interwoven elements). Further, the geometry (e.g., roughness, location, direction, and size of ridges) of the external body surface 106 could be more complicated than the smooth surface illustrated in FIG. 1, and one or more properties of this surface could have some effect on the sensitivity of the optical device to a property of interest of the POSV 108. A target tissue could be a specific location within a layer of tissue (e.g., a specific subsection of and/or volume within the PSOV 108). Accordingly, the device 100 could be configured and/or operated to detect the specific location and/or to optically detect the property of interest of the specific location (e.g., by operating one or more actuator of the device 100 to change the location of the device 100 and/or elements thereof, to specify a field of view of the light sensor 120 such that the light sensor 120 detects light form the specific location). Additionally or alternatively, the device 100 could indicate to a user to reposition the device relative to a detected location of the specific location within the layer of tissue.

The device 100 could include a housing, a mount, an armature, or some other additional elements according to an application. For example, the device 100 could be incorporated into a wearable device, and the wearable device could include a mount (e.g., a strap) configured to securely position the device 100 relative to the POSV 108 or some other target tissue (e.g., by securing the device 100 around a wrist of a user such that the PSOV 108 is observable by the optical device). The device 100 could be part of a medical imaging apparatus (e.g., part of an MRI, X-ray imager, fluorescent imager, or some other apparatus configured to image anatomy and/or physiology of a patient) or some surgical equipment (e.g., could be configured to provide information to guide a surgical intervention). The device 100 could be part of a tabletop device and/or a wired or wireless handheld device.

Further, the device 100 could include additional elements according to an application. For example, the device 100 could include a user interface configured to indicate a detected property of interest of the POSV 108 or to indicate some other information. Such a user interface could be further configured to received inputs form a user, e.g., inputs commanding the device 100 to perform measurement, to input some relevant information about a subject of the device (e.g., a weight, a skin type, a target body part), or to input some other information to the device 100. Additionally or alternatively, the device 100 could include a communication interface configured to enable communication between the device 100 and some remote system (e.g., a server). Other additional or alternative elements and configurations of the device 100 are anticipated.

III. Illustrative Operating Modes

Operating modes of an optical device describe the configuration and/or operation of elements of the optical device to perform an optical interrogation of a target, i.e., to illuminate the target and detect light responsively emitted by the target in order to determine and/or detect a property of the target. Operating modes can describe the configuration of elements of the optical device (e.g., the location and orientation of elements of the optical device relative to each other and/or the target environment, the presence of filters or other optical components in an optical path of the optical device) and/or the operation of elements of the optical device (e.g., the intensity of light emitted by a light source, the operation to become opaque of a set of pixels of a spatial light modulator, the selection of a set of pixels of a multipixel light sensor related to a specified field of view of the light sensor, an integration time of a photodetector). Operational modes can be defined continuously (e.g., can be defined as continuous functions of an input variable) or can be discretely defined (e.g., as elements of a lookup table, as a discrete set of operational states corresponding to respective discrete input values and/or respective ranges of values of a continuous input).

Operational modes could be specified such that operation of the optical device according to a selected operational mode is in some way optimized. For example, a sensitivity, an accuracy, a signal-to-noise ratio, noise spectrum, a minimum detectable change, a repeatability, or other properties of a property of a target that is detected and/or determined using the optical device could be maximized. One or more such properties could be used to define a figure of merit (FOM) and operational modes could be determined and/or specified to maximize the FOM when the optical device is operated to detect a property of interest of a target tissue. Operational modes could be determined or specified to maximize the FOM given one or more constraints, parameters, or other properties of the optical device, the target, and/or elements of the environment of the target (e.g., an intervening tissue or other material disposed between the optical device and the target).

For example, an individual operational mode could describe or specify a first configuration and/or operation of an optical device (e.g., a beam width, a field of view) that maximizes an FOM of detection of a property of interest of a target tissue when an intervening tissue between the optical device and the target tissue has a first thickness. A further individual operational mode could describe or specify a second configuration and/or operation of the optical device that maximizes the FOM of detection of the property of interest when the intervening tissue has a second thickness. A plurality of such operational modes could be determined and/or specified for a range of conditions (e.g., a range of intervening tissue thicknesses) and could be selected relative to a detected condition (e.g., an operational mode comprising an element of a look-up table could be selected corresponding to a value of detected intervening tissue thickness). Additionally or alternatively, an operational mode could be determined, based on a detected or determined condition (e.g., a detected intervening tissue thickness), using a specified and/or determined formula, equation or other algorithm (e.g., a calibration curve could be determined relating intervening tissue thickness to the diameter of a beam of illumination, and such a curve could be used to determine an operational mode, such as a diameter of the beam of illumination, based on a detected intervening tissue thickness). Operational modes could specify additional or alternative parameters of the configuration and/or operation of an optical device based on additional or alternative properties of a target, the environment of the target, the optical device, or some other factor(s).

Operational modes and related information (e.g., look-up tables, calibration curves, etc.) could be determined in a variety of ways such that operating an optical device according to a selected operational mode maximizes some FOM of a detected property of interest of a target. In some examples, a series of experiments and/or simulations could be performed to determine the FOM across a variety of configurations and/or operations of the optical device, the target and/or elements or materials in the environment of the target. Operational modes could be determined, based on such experiments and/or simulations, such that the FOM is maximized across some set of conditions.

An elementary simulation is an individual simulated operation of an optical device to detect a target property of a target. An individual elementary simulation is defined by a set of parameters describing the configuration of the target and its environment (e.g., defining the thickness, geometry, optical properties (e.g., autofluorescence cross-sections, scattering coefficients, absorption spectra, excitation spectra, emission spectra, extinction coefficients), or other information about a target tissue, an intervening tissue located between the target tissue and an external body surface, and/or some other tissues or other elements in the environment of the target). The individual elementary simulation is further defined by parameters describing the configuration and/or operation of the simulated optical device to detect the property of interest of the target (e.g., wavelengths of illumination and/or detection, beam widths of illumination, beam shapes of illumination, intensities of illumination, fields of view of light detection, focal lengths of light detection/emission, exposure times of light detection).

Such parameters of an elementary simulation could describe the configuration and/or operation of the optical device directly (e.g., could specify a set of pixels of a multipixel light sensor to use). Additionally or alternatively, such parameters could describe features of the detection of the property of interest (e.g., could specify a field of view relative to a target tissue; a set of pixels of a multipixel light sensor related to the specified field of view could be determined based on the specified field of view). An individual elementary simulation could allow the determination of the FOM corresponding to the configuration and/or operation of the optical device and of the configuration of the target and its environment. For example, an elementary simulation could simulate a number of noise sources in the target, the target's environment, and the optical device, and an FOM (e.g., a sensitivity of the optical device to a property of interest of the target) could be determined based on the elementary simulation. Additionally or alternatively, a set of elementary simulations could be performed to determine an FOM corresponding to a particular set of parameters by varying some other parameter(s) (e.g., performing a set of elementary simulations wherein a level of the property of interest of the target is varied in order to determine a corresponding variation in a signal detected and/or output by the optical device).

An individual elementary simulation could be performed in a variety of ways related to the configuration of the simulation. In some examples, the target and/or its environment could include a turbid or otherwise light-scattering material (e.g., a biological material that includes blood cells, epithelial cells, skin cells, or other light-scattering cells or materials). In such examples, an individual elementary simulation could include performing many simulations of the scattering of individual simulated photons by the light-scattering material to determine a FOM corresponding to the parameters of the elementary simulation. Such repeated simulations could be performed according to a Monte-Carlo or other statistical simulation paradigm. For example, a set of photons emitted by the optical device could be pseudo-randomly generated (e.g., according to a distribution relating to a beam location, orientation, width, shape, wavefront, or other parameters of the configuration and/or operation of the optical device) and the scattering of the generated photons by the light-scattering material could be simulated to generate an overall simulation of the operation of the optical device to optically interrogate the target.

Properties and/or parameters of the elementary simulations and models related thereto (e.g., models of a target tissue and an intervening tissue, models of the optical device) could be specified relative to an application. For example, in applications wherein the location, concentration, or other properties of fluorophores (e.g., fluorophores of a contrast agent configured to selectively interact with an analyte of interest) in a portion of subsurface vasculature are to be detected, the simulations could model an absorbance cross-section, a number and/or spatial distribution of fluorophores within the portion of subsurface vasculature, an excitation spectrum, an emission spectrum, a quantum efficiency, or some other properties of the fluorophores. Other additional or alternative model properties related to additional applications (e.g., detection of additional properties of various targets) are anticipated.

A plurality of elementary simulations could be performed, having a plurality of respective parameter sets describing properties of simulated optical devices, targets, and other elements of the environment of the targets, to determine respective figures of merit (FOMs) of optical detection of a property of interest of the targets. Such a plurality of simulations (along with their corresponding parameters and FOMs) could be used to determine operational modes of an optical device to, e.g., maximize the FOM of detected properties of interest of targets (e.g., of target subsurface tissues of a user) detected using the optical device. For example, parameters of configuration and/or operation of the optical device corresponding to an elementary simulation having the greatest FOM of the plurality of elementary simulations could be used to define an operational mode of the optical detector.

Alternatively, a plurality of operational modes corresponding to a respective plurality of configurations of the target and the environment of the target could be determined. This could include performing a plurality of simulations across which the simulation parameters describing the target (e.g., of a target tissue) and environment of the target (e.g., properties of an intervening tissue between a target tissue and an external body surface) are constant and the parameters describing the configuration and/or operation of the optical device are different. A simulation of the plurality of simulations having the greatest FOM could be selected and used to define an operational mode. An optical device could be operated according to the operational mode responsive to a determination that a target and/or environment of the optical device corresponded to the simulation parameters describing the target and environment of the target of the plurality of simulations. By extension, a plurality of operational modes corresponding to a plurality of configurations of a target and/or environment of a target could be determined.

In some examples, a plurality of elementary simulations could be performed to 'span' a space of parameters describing a target of an optical detector and/or an environment thereof. For each particular set of parameters describing the target and/or environment (e.g., each 'point' in the spanned space of parameters), a configuration and/or operation of the optical detector could be determined to maximize a FOM of detection of a property of interest of the target by the optical device (e.g., by performing a further plurality of simulations using the particular set of parameters describing the target and/or environment and a further set of parameters describing the configuration and/or operation of the optical device). Operational modes of the optical device (e.g., modes relating to and/or defined by calibration curves, discrete sets of configurations and/or operations of elements of the optical device) could be determined based on the plurality of elementary simulations.

In some examples, patterns of dependence between parameters of the simulated target and/or environment thereof and corresponding FOM-maximizing parameters of the configuration and/or operation of the optical device could be determined and used to specify calibration curves or other elements defining operational modes of the optical device. Such relationships could be detected using dimensionality-reduction techniques (e.g., principal components analysis, independent components analysis, ISOMAP, non-negative matrix factorization) or some other methods. Additionally or alternatively, parameter sets for simulations could be specified to investigate relationships between parameters of the target and/or environment that can be easily, accurately, and/or cheaply detected (e.g., thicknesses of tissues, colors of tissues) and parameters of the configuration and/or operation of an optical device that can be easily and or cheaply controlled (e.g., by changing an electronic operation of one or more components of the optical device, by including one or more actuators to control a location, orientation, or other mechanical configuration of one or more elements of the optical device).

Operational modes could be described and/or defined in a variety of ways. Operational modes could be defined as the output of one or more functions, functionals, look-up tables, transformations, or other algorithms or methods of determination. Such outputs could specify one or more parameters of configuration and/or operation of the optical device (e.g., properties of illumination emitted by the optical device toward a target, properties of the detection of light from the target). Such operational mode selection could be performed based on one or more detected properties of a target and/or environment thereof. Selected operational modes and/or aspects thereof could be continuous-valued (i.e., could have a continuous range of possible values) or discrete (i.e., could have possible values and/or configurations selected from a discrete set of possible output values and/or configurations).

Figure 2A:
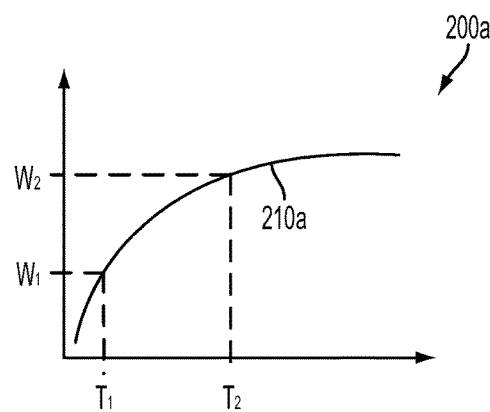
FIG. 2A is an example of a calibration curve.

FIG. 2A illustrates an example continuous relationship 200a between a property of a target and/or environment of an optical detector (along the horizontal axis) and a property of the configuration and/or operation of the optical device (vertical axis) corresponding to a maximum-FOM detection of a property of interest of the target by the optical detector. The relationship 200a is defined by a calibration curve 210a that relates an input value of the property of the target and/or environment to an output value of a property of the configuration and/or operation of the optical device. For example, the input property could be a detected thickness of an intervening tissue disposed between a target tissue and an external body surface, and the output property could be a width of a beam of illumination emitted by the optical device through the external body surface and the intervening tissue into the target tissue. Thus, the calibration curve 210a could be used to generate a first output beam width $W_1$ based on a first detected thickness $T_1$. Similarly, the calibration curve 210a could be used to generate a second output beam width $W_2$ based on a second detected thickness $T_2$ that is different from the first detected input thickness $T_1$. The calibration curve 210a could be a continuous function, a discontinuous function, a piece-wise defined function, a polynomial, a Taylor expansion, a sinusoid, a Fourier expansion, an exponential, a hyperbolic, or some other type of relation and/or combination of relations (e.g., a sum of a polynomial and an exponential).

Figure 2B:
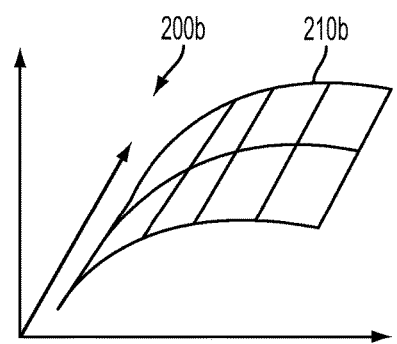
FIG. 2B is an example of a calibration curve.

FIG. 2B illustrates an example continuous relationship 200b between two properties of a target and/or environment of an optical detector (along the horizontal and into-the-page axes) and a property of the configuration and/or operation of the optical device (vertical axis) corresponding to a maximum-FOM detection of a property of interest of the target by the optical detector. The relationship 200b is defined by a calibration surface 210b that relates input values of the properties of the target and/or environment to an output value of a property of the configuration and/or operation of the optical device. For example, the input properties could be a detected thickness and a detected melanin content of an intervening tissue disposed between a target tissue and an external body surface, and the output property could be a width of a beam of illumination emitted by the optical device through the external body surface and the intervening tissue into the target tissue. The calibration surface 210b could be a continuous function, a discontinuous function, a piece-wise defined function, a polynomial, a Taylor expansion, a sinusoid, a Fourier expansion, an exponential, a hyperbolic, or some other type of relation and/or combination of relations (e.g., a sum of a polynomial and an exponential).

Figure 3:
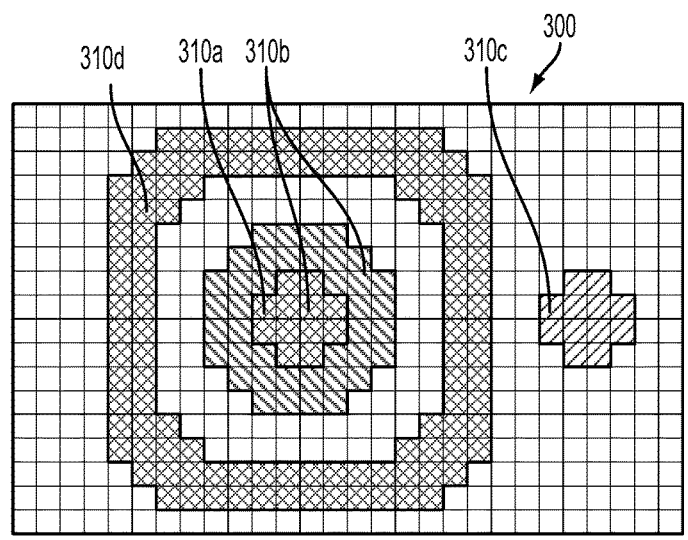
FIG. 3 illustrates example sets of pixels of a multipixel imager.

FIG. 3 illustrates a set of pixels 300 of a multipixel photodetector of an optical device as described herein. Such a multipixel photodetector could be operated to image a target of the optical detector (e.g., to generate an image corresponding to the spatial patterns of light emitted by the target and received by the optical detector). Additionally or alternatively, pixels of the multipixel photodetector could be grouped and corresponding pixel outputs could be used (e.g., summed, combined according to a weighted average, or some other method) to generate a single output related to the light received by the pixels of the set of pixels. For example, sets of pixels of the multipixel photodetector could be grouped such that the multipixel photodetector acted as a single photodetector having a field of view related to the selected set of pixels (e.g., related to a spanned range of angles within the total field of view of the multipixel photodetector corresponding to light within the spanned range of angles received by the pixels of the selected set of pixels). For example, first pixel set 310a illustrates a set of pixels that could be selected corresponding to a first field of view near the center of the overall field of view of the multipixel photodetector.

The field of view could be widened by increasing the set of pixels in the set of selected pixels. For example, second pixel set 310b illustrates a set of pixels that could be selected corresponding to a second field of view near the center of the overall field of view of the multipixel photodetector. The second pixel set 310b includes the pixels of the first pixel set 310a such that the second field of view is broader than the first field of view.

The field of view could be relocated by selecting a set of pixels in a different location in the multipixel photodetector. For example, third pixel set 310c illustrates a set of pixels that could be selected corresponding to a third field of view toward the edge of the overall field of view of the multipixel photodetector. The third pixel set 310c includes a similarly sized and shaped set of pixels as the first pixel set 310a displaced across the multipixel array such that the third field of view is displaced relative to the first field of view.

Fields of view and related fields of view could be specified in different ways and have corresponding different shapes. In some examples, the field of view could correspond to photons received by the optical device within a specified range of angles from a central axis or other specified direction of the optical device. For example, fourth pixel set 310d illustrates a ring-shaped set of pixels that could be selected corresponding to a fourth field of view corresponding to a range of angles relative to a central optical axis of the multipixel photodetector. The diameter, thickness, or other properties of the fourth pixel set 310*d* within the multipixel photodetector could be related to properties of the corresponding field of view (e.g., the thickness of the ring could be related to the magnitude of the range of angles of the view of view). Such a field of view could be selected to detect light emitted from a target in response to illumination that includes photons that have a certain statistical distribution of number of scatterings within the target, path length, or some other property, that correspond to a certain depth within the target, that correspond to a certain focus, or according to some other application.

Operational modes of an optical device could specify sets of pixels of a multipixel photodetector (e.g., 310*a*, 310*b*, 310*c*, 310*d*) or of some other set of discrete elements of the optical device (e.g., sets of pixels of a spatial light modulator, light emitters of an array of light emitters). Additionally or alternatively, operational modes could specify a field of view or other property of the operation and/or configuration of an optical device, and a model, look-up table, or other method could be used to determine a set of pixels (or other elements from a set of secrete elements) related to the specified field of view or other property. For example, a field of view diameter of an operational mode could be selected based on the output of a calibration curve (e.g., the calibration curve could receive an intervening tissue thickness as an input and could output a field of view diameter in millimeters, radians, degrees, steradians, or some other units) and a corresponding set of pixels could be selected based on the selected field of view diameter. Other operations of an optical device to select, weight, or otherwise operate elements of a discrete set of elements of the optical detector are anticipated.

Operational modes of an optical device as descried herein could be defined by one or more calibration curves, look-up tables, discrete parameter sets and/or discrete sets of elements of the optical device. For example, an operational mode could be selected by (a) using a calibration curve to determine the diameter of an emitted beam of illumination based on a detected intervening tissue thickness and (b) selecting a set of pixels of a multipixel photodetector from a discrete set of such sets by selecting the set corresponding to a range of skin melanin content values containing a detected skin melanin content of the intervening tissue. Further, operational modes could be selected based on information input by a user of the optical device (e.g., information relating to the user's age, skin type, body mass index, or other information).

In a particular example, an optical device could be configured to detect oxygen saturation of blood in a portion of arterial subsurface vasculature. An operational mode defining an illumination beam shape and/or a detector field of view could be selected based on a detected depth of the arterial subsurface vasculature beneath an external body surface. In another particular example, an optical device could be configured to detect fluorophores (e.g., fluorophores configured to selectively interact with an analyte of interest) in a portion of subsurface vasculature. An operational mode defining an illumination beam shape and/or a detector field of view could be selected based on a detected thickness of an intervening tissue between the portion of subsurface vasculature and an external body surface.

IV. Example Devices

Optical devices and other embodiments as described herein can be incorporated into a variety of devices or systems. For example, an optical device could be part of a desktop or other relatively immobile apparatus and a biological environment of interest (e.g., an arm of a wearer) could be brought into proximity with the optical device. Additionally or alternatively, an optical device could be part of a wireless or wired handheld device (e.g., a handheld optical probe), and a user of the device could position the optical probe in proximity to an environment of interest. Optical devices as described herein could be part of medical diagnostics and imaging systems, surgical apparatus (e.g., part of an apparatus configured to allow an image-guided surgical intervention), scientific equipment, or other systems. In some examples, an optical device and associated components (e.g., a detector configured to determine a property of an intervening tissue between a target tissue and an external body surface) could be part of a wearable device that is configured to be mounted, positioned, or otherwise worn on a body part of a user (e.g., around a user's wrist).

Figure 4:
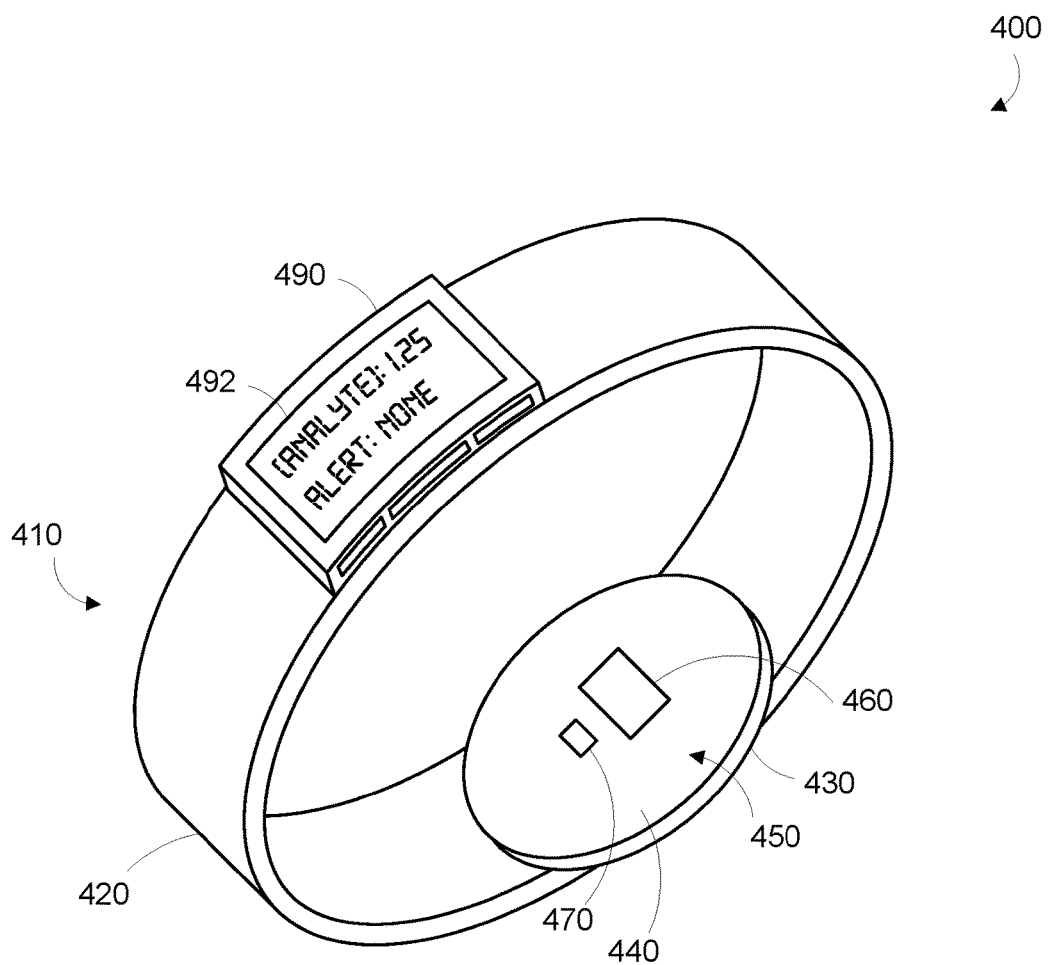
FIG. 4 is a perspective view of an example wearable device.

A wearable device 400 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements of a target tissue in a non-invasive manner from outside of the body, the wearable device may be positioned on a portion of the body where the target tissue (e.g., a portion of subsurface vasculature) is easily observable, the qualification of which will depend on the type of detection system used. The device may be placed in close proximity to the skin or tissue, but need not be touching or in intimate contact therewith. A mount 410, such as a belt, wristband, ankle band, etc. can be provided to mount the device at, on or in proximity to the body surface. The mount 410 may prevent the wearable device from moving relative to the body to reduce measurement error and noise. In one example, shown in FIG. 4, the mount 410, may take the form of a strap or band 420 that can be worn around a part of the body. Further, the mount 410 may be an adhesive substrate for adhering the wearable device 400 to the body of a wearer.

A measurement platform 430 is disposed on the mount 410 such that it can be positioned on the body where subsurface vasculature or some other target tissue is easily observable. An inner face 440 of the measurement platform is intended to be mounted facing to the body surface. The measurement platform 430 may house a data collection system 450, which includes an optical device 460 for optically detecting at least one physiological parameter of the target tissue through an intervening tissue disposed between the target tissue and an external body surface (e.g., skin and other connective tissue disposed between a target portion of subsurface vasculature and an overlying skin surface). Such physiological parameters could include any parameters that may relate to the health of the person wearing the wearable device. For example, the optical device 460 could be configured to measure blood volume, blood oxygenation fraction, pulse rate, the presence of one or more analytes in tissue (e.g., of fluorescent analytes and/or contrast agents in the tissue), or some other property.

The optical device 460 includes a light source configured to illuminate the target tissue through the external body surface and the target tissue and a light sensor configured to detect light through the intervening tissue and external body surface that is emitted from the target tissue in response to illumination by the light source. The components of the data collection system 450 may be miniaturized so that the wearable device may be worn on the body without significantly interfering with the wearer's usual activities.

The light sensor may include CMOS, CCD, photodiode, phototransistor, or other optically sensitive elements or combinations thereof. The light sensor could include one or more filters configured to block specified ranges of wavelengths of light from being received by light-sensitive elements of the light sensor. The light sensor could be configured to sense the polarization of light and/or to only detect light of a specified polarization. For example, the light sensor could include a linear polarization filter such that the light sensor only detects light having a polarization aligned with the orientation of the linear polarization filter. The light sensors could be configured to detect one or more properties of light emitted by a fluorophore, a color center in a nanodiamond, a Raman dye, a chemiluminescent material, a bioluminescent material, or some other light emitting substance. The light sensor could be configured to include multiple light sensitive elements configured to detect respective lights having wavelengths within respective ranges.

The optical device 460 further includes a light source for transmitting illumination that can penetrate the wearer's skin (i.e., external body surface and intervening tissue) into the target tissue, for example, into a lumen of a portion of subsurface vasculature. The transmitted illumination can be any kind of illumination that is benign to the wearer and that results at least in responsive emission of light by the target tissue that is related to a physiological property of interest of the target tissue. In some examples, the transmitted illumination could have a wavelength specified to correspond to an absorption wavelength of a fluorophore or other fluorescent element of or in the target tissue. The wavelength of the transmitted illumination could be specified to penetrate biological tissues of a wearer; for example, the transmitted illumination could have a wavelength within one or both of the near-infrared (NIR) transparency windows of biological tissue. In some examples, the illumination could include coherent light (e.g., the light source could include a coherent light source like a laser).

The optical device 460 could be operated in such a manner as to maximize its sensitivity to the at least one physiological parameter of the target tissue. This could include configuring and/or operating one or more elements of the optical device 460 (e.g., of the light source and light sensor) in a manner that maximizes the optical device's 460 sensitivity to the at least one physiological parameter given at least one detected other property of the intervening tissue and/or target tissue (e.g., a thickness of one or more layers of intervening tissue, a scattering coefficient, a color, an extinction coefficient, a melanin content, a structure of subsurface vasculature within the intervening and/or target tissue). Such a detected other property could be detected using the optical device 460 or using detector 470. Configuring and/or operating one or more elements of the optical device 460 could include operating the optical device 460 according to an operational mode that is selected based on the detected other property, e.g., controlling a beam width, field of view, focus, or other property of the optical device 460 to have a value or configuration corresponding to a detected value of the other property of the intervening and/or target tissues.

Operating the optical device 460 according to an operational mode could include configuring and/or operating the light source, light sensor, and/or other elements of the optical device 460 in a variety of ways. In some examples, a wavelength, a spectral profile, a beam width, a beam shape, a coherence width, a pulse width, an intensity, a beam location and/or angle, a wavefront shape, and/or some other property or combination of properties of illumination emitted by the light source could be controlled according to the operational mode (e.g., by operating a beam shaper of the light source according to the operational mode). In some examples, an integration time, a field of view, a wavelength(s) of sensitivity, a degree of amplification, a focal length, a color or other filter setting, and/or some other property or combination of properties of the light sensor and the use thereof to detect light from the target tissue could be controlled according to the operational mode. Operating the optical device 460 according to an operational mode could include specifying the operation of electronic parameters of the optical device 460 (e.g., of the light source and/or light sensor). Additionally or alternatively, operating the optical device 460 according to an operational mode could include operating actuators, servos, or other actuators to control a configuration of elements of the optical device 460 (e.g., to alter a configuration of optics (e.g., to change a focal length), to change the relative location and/or angle of the light source relative to the light detector and/or optics of the optical device 460).

The detector 470 could be configured in a variety of ways to detect a variety of other properties of the intervening and/or target tissues. For example, the detector 470 could include an acoustical transducer, an optical coherence tomography (OCT) sensor, a visible light camera, an infrared camera, or some other components configured to detect a thickness of the intervening tissue, a depth of the target tissue beneath the external body surface (i.e., beneath surface of the wrist of a wearer), or some other property of the location, thickness, and/or other properties of various elements and tissues of a wearer. The detector 470 could be additionally or alternatively configured to detect a temperature, a scattering coefficient, an extinction coefficient, an absorbance spectrum, a water content and/or hydration level, a color, a melanin content, a fat content, or some other property or properties of the intervening tissue, the target tissue, and or some other tissues of a wearer and/or some other biological environment.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of the measured physiological parameters, for instance, the concentrations of certain analytes being measured in the tissue, the oxygen saturation of blood, or some other physiological parameters.

Figure 5A:
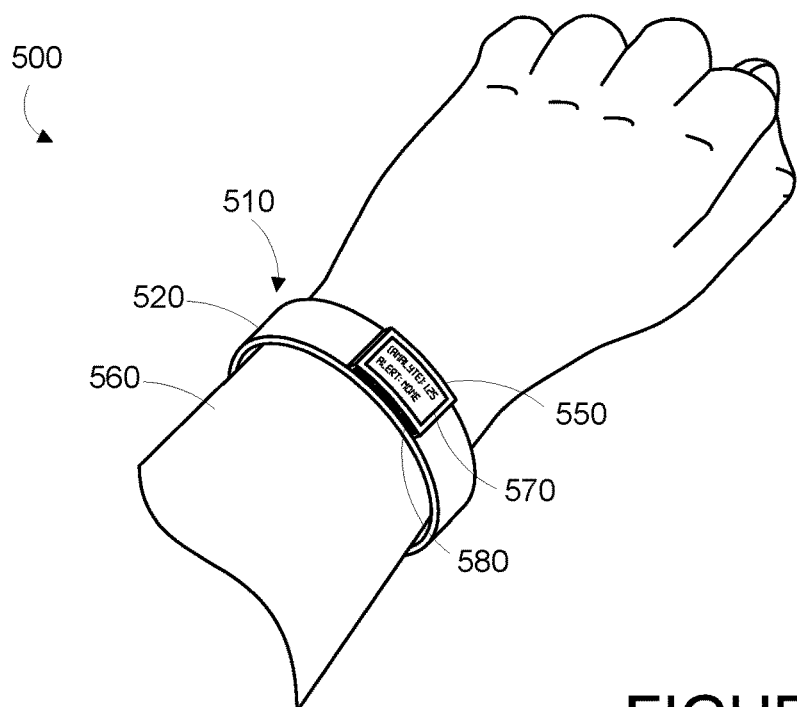
FIG. 5A is a perspective top view of an example wrist-mounted device, when mounted on a wearer's wrist.
Figure 5B:
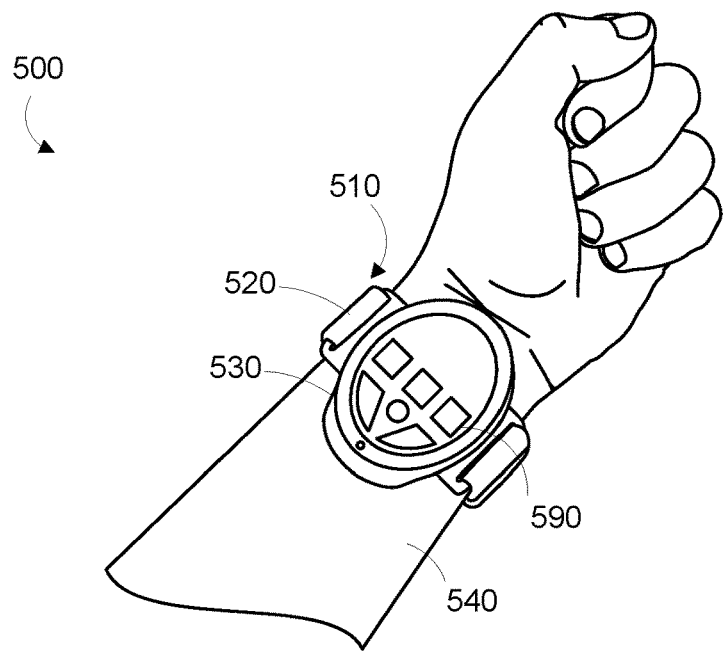
FIG. 5B is a perspective bottom view of an example wrist-mounted device shown in FIG. 5A, when mounted on a wearer's wrist.

In one example, the wearable device is provided as a wrist-mounted device, as shown in FIGS. 5A, 5B, and 6A-6C. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a measurement platform 530 positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the measurement platform 530 may be located on the anterior side 540 of the wearer's wrist where a portion of subsurface vasculature or some other target tissue may be readily observable through intervening tissues (e.g., skin, connective tissues) between the target tissue and an overlying external body surface (e.g., the posterior side 560 of the wearer's wrist). However, other configurations are contemplated.

The display 570 may be configured to display a visual indication of the alert or recommendation and/or an indication of the measured physiological parameters, for instance, the presence or concentrations of certain analytes in the target tissue being measured. Further, the user interface 550 may include one or more buttons 580 for accepting inputs from the wearer. For example, the buttons 580 may be configured to change the text or other information visible on the display 570. As shown in FIG. 5B, measurement platform 530 may also include one or more buttons 590 for accepting inputs from the wearer. The buttons 590 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 6A:
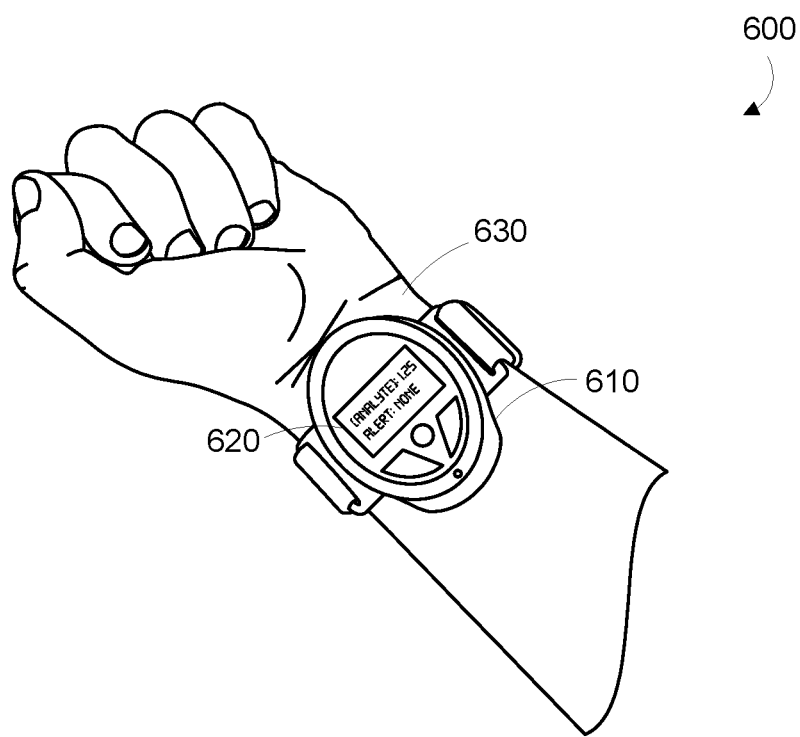
FIG. 6A is a perspective bottom view of an example wrist-mounted device, when mounted on a wearer's wrist.
Figure 6B:
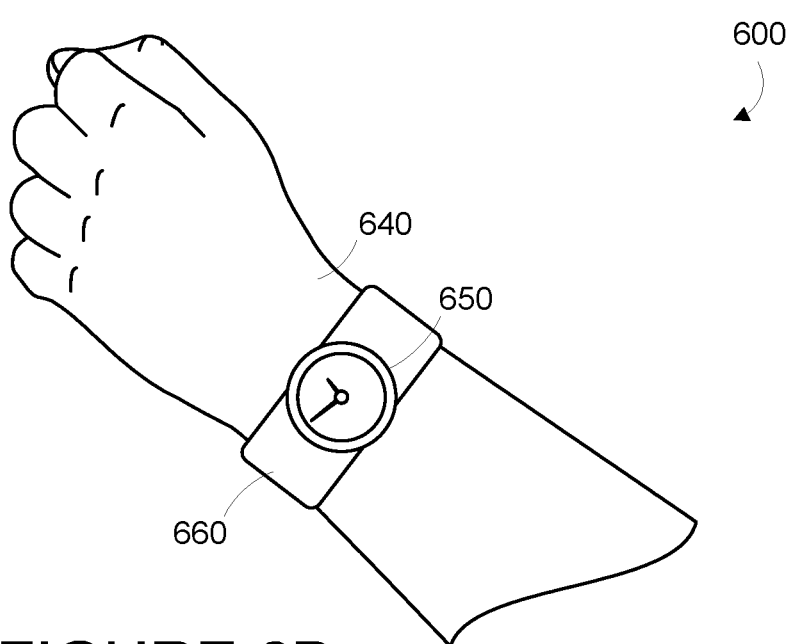
FIG. 6B is a perspective top view of an example wrist-mounted device shown in FIG. 6A, when mounted on a wearer's wrist.
Figure 6C:
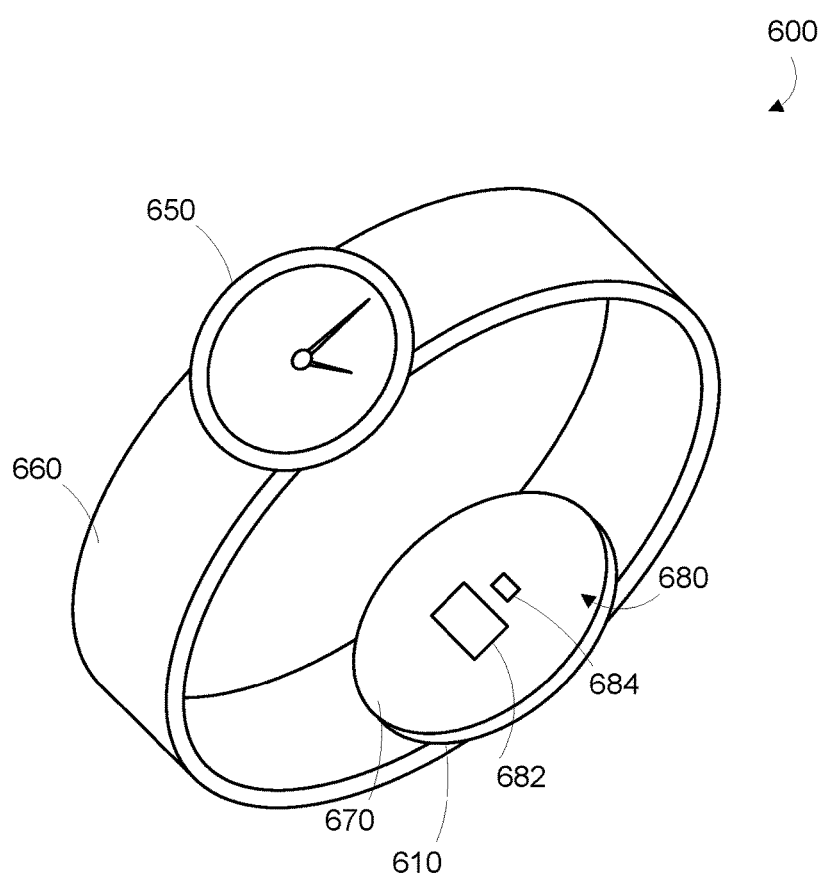
FIG. 6C is a perspective view of an example wrist-mounted device shown in FIGS. 6A and 6B.

In another example wrist-mounted device 600, shown in FIGS. 6A-6C, the measurement platform 610 and user interface 620 are both provided on the same side of the wearer's wrist, in particular, the anterior side 630 of the wrist. On the posterior side 640, a watch face 650 may be disposed on the strap 660. While an analog watch is depicted in FIG. 6B, one of ordinary skill in the art will recognize that any type of clock may be provided, such as a digital clock.

As can be seen in FIG. 6C, the inner face 670 of the measurement platform 610 is intended to be worn proximate to the wearer's body. A data collection system 680 housed on the measurement platform 610 may include an optical device 682 and a detector 684. The optical device 682 is configured to, through an external body surface (e.g., surface of the wrist of a wearer) and an intervening tissue between a target tissue and the external body surface, illuminate a target tissue and to detect light emitted responsively from the target tissue due to the illumination. The optical device 682 is configured to be operated according to one or more operational modes to detect a property of interest of the target tissue. The detector is configured to detect one or more properties of the intervening tissue and/or target tissue that are related to the sensitivity of the optical device 682 to the property of interest. An operational mode of the optical device 682 could be selected based on the output of the detector 684 to maximize the sensitivity of the optical detector 682 to the property of interest.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

V. Example Electronics Platform for a Device

Figure 8:
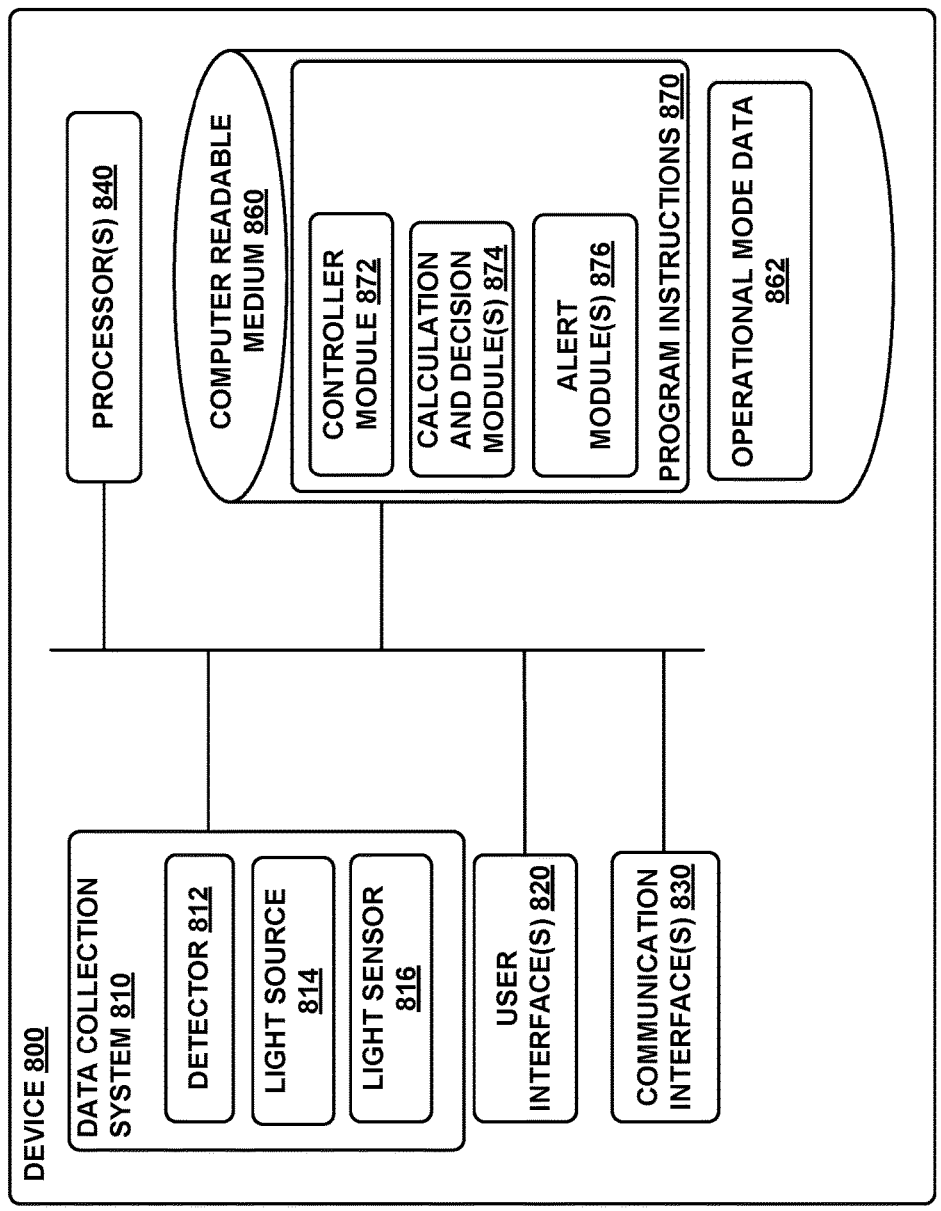
FIG. 8 is a functional block diagram of an example device.

FIG. 8 is a simplified block diagram illustrating the components of a device 800, according to an example embodiment. Device 800 may take the form of or be similar to one of the wrist-mounted devices 400, 500, 600 shown in FIGS. 4, 5A-B, and 6A-3C, or the device 100 shown in FIG. 1. Device 800 may also take other forms, such as an ankle, waist, or chest-mounted device. Device 800 could also take the form of a device that is not configured to be mounted to a body. For example, device 800 could take the form of a handheld device configured to be maintained in proximity to a biological environment of interest (e.g., a body part, a biological sample container) by a user or operator of the device 800 or by a frame or other supporting structure. Device 800 could also take the form of a device configured to illuminate and to detect emitted light from a target region within an in vitro biological environment or some other environment, for example, a fluid volume within a water treatment process. Device 800 could be configured as or part of a microscope, fluorescence microscope, confocal microscope, two-photon microscope, multi-photon microscope, total internal reflection fluorescence microscope, or some other laboratory equipment. Device 800 also could take other forms.

In particular, FIG. 8 shows an example of a device 800 having a data collection system 810, a user interface 820, communication interface 830 for transmitting data to a remote system, and processor(s) 840. The components of the wearable device 800 may be disposed on a mount or on some other structure for mounting the device to an external body surface where a target tissue (e.g., a portion of subsurface vasculature) is readily optically observable through the external body surface and an intervening tissue disposed between the target tissue and the external body surface.

Processor 840 may be a general-purpose processor or a special purpose processor (e.g., digital signal processors, application specific integrated circuits, etc.). The one or more processors 840 can be configured to execute computer-readable program instructions 870 that are stored in the computer readable medium 860 and that are executable to provide the functionality of a device 800 described herein. The one or more processors 840 can be configured to access operational mode data 862 that are stored in the computer readable medium 860 and that describe operational modes of the light source 814 and light sensor 816 to optically detect properties of a target tissue.

For example, operational mode data 862 could describe configurations (e.g., focal lengths of optics, locations and/or orientations of beams of illumination emitted by the light source 814) and/or operations (e.g., illumination intensities, pulse widths, integration times, set of pixels of a multipixel sensor) of the light source 814 and/or light sensor 816 that could be selected (e.g., by the processor 840 according to instructions of the program instructions 870) to allow for maximum sensitivity detection of a property of the target tissue. Such selection could be performed relative to a detected other property of the target tissue and/or of an intervening tissue disposed between the target tissue and an external body surface (e.g., of skin and/or connective tissue) detected using, e.g., the detector 812 and/or the light source 814 and light sensor 816.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

The data collection system 810 includes a light source 814 and light sensor 816 (collectively comprising an optical device) for optically detecting at least one physiological parameter of the target tissue through an intervening tissue disposed between the target tissue and an external body surface (e.g., skin and other connective tissue disposed between a target portion of subsurface vasculature and an overlying skin surface). Such physiological parameters could include any parameters that may relate to the health of a person wearing or otherwise using the device 800. For example, the light source 814 and light sensor 816 could be configured to measure blood volume, blood oxygenation fraction, pulse rate, the presence of one or more analytes in tissue (e.g., of fluorescent analytes and/or contrast agents in the tissue), or some other property. The data collection system 810 further includes a detector 812 configured to detect one or more other properties of the target tissue and/or the intervening tissue that are related to the sensitivity of the optical device to the at least one physiological parameter of the target tissue.

The light source 814 is configured to illuminate the target tissue through the external body surface and the target tissue and the light sensor 814 is configured to detect light through the intervening tissue and external body surface that is emitted from the target tissue in response to illumination by the light source 814. The components of the data collection system 810 may be miniaturized so that the device 800 may be worn on a body without significantly interfering with a wearer's usual activities.

The light sensor 816 may include CMOS, CCD, photodiode, phototransistor, or other optically sensitive elements or combinations thereof. The light sensor 816 could include one or more filters configured to block specified ranges of wavelengths of light from being received by light-sensitive elements of the light sensor 816. The light sensor 816 could be configured to sense the polarization of light and/or to only detect light of a specified polarization. For example, the light sensor 816 could include a linear polarization filter such that the light sensor 816 only detected light having a polarization aligned with the orientation of the linear polarization filter. The light sensor 816 could be configured to detect one or more properties of light emitted by a fluorophore, a color center in a nanodiamond, a Raman dye, a chemiluminescent material, a bioluminescent material, or some other light emitting substance. The light sensor 816 could be configured to include multiple light sensitive elements configured to detect respective lights having wavelengths within respective ranges.

The light source 814 is configured to transmit illumination that can penetrate the external body surface and intervening tissue into the target tissue, for example, into a lumen of a portion of subsurface vasculature. The transmitted illumination can be any kind of illumination that is benign to a wearer or other user and that results at least in responsive emission of light by the target tissue that is related to a physiological property of interest of the target tissue. In some examples, the transmitted illumination could have a wavelength specified to correspond to an absorption wavelength of a fluorophore or other fluorescent element of or in the target tissue. The wavelength of the transmitted illumination could be specified to penetrate biological tissues of a wearer; for example, the transmitted illumination could have a wavelength within one or both of the near-infrared (NIR) transparency windows of biological tissue. In some examples, the illumination could include coherent light (e.g., the light source 814 could include a coherent light source like a laser).

The light source 814 and light sensor 816 could be operated (e.g., by the processor 840 executing program instructions 870) in such a manner as to maximize the sensitivity of detection of the at least one physiological parameter of the target tissue. This could include configuring and/or operating one or more elements of the light source 814 and light sensor 816 in a manner that maximizes the optical device's sensitivity to the at least one physiological parameter given at least one detected other property of the intervening tissue and/or target tissue (e.g., a thickness of one or more layers of intervening tissue, a scattering coefficient, a color, an extinction coefficient, a melanin content, a structure of subsurface vasculature within the intervening and/or target tissue). Such a detected other property could be detected using the optical device and/or using the detector 812. Configuring and/or operating one or more elements of the optical device could include operating the optical device (e.g., as described by instructions of the controller module 872) according to an operational mode described in the operational mode data 862 that is selected based on the detected other property (e.g., as described by instructions of the controller module 872 and/or the calculation and decision modules(s) 874). For example, the operational mode data 862 could describe and/or specify controlling a beam width, field of view, focus, or other property of the optical device to have a value or configuration corresponding to a detected value of the other property of the intervening and/or target tissues.

Operating the optical device according to an operational mode described in the operational mode data 862 could include configuring and/or operating the light source 814, light sensor 816, and/or other elements of the data collection system 810 in a variety of ways. In some examples, a wavelength, a spectral profile, a beam width, a beam shape, a coherence width, a pulse width, an intensity, a beam location and/or angle, a wavefront shape, and/or some other property or combination of properties of illumination emitted by the light source 814 could be controlled according to a selected operational mode (e.g., by operating a beam shaper of the light source according to the operational mode). In some examples, an integration time, a field of view, a wavelength(s) of sensitivity, a degree of amplification, a focal length, a color or other filter setting, and/or some other property or combination of properties of the light sensor 816 and the use thereof to detect light from the target tissue could be controlled according to the selected operational mode. Operating the optical device according to an operational mode could include specifying the operation of electronic parameters of the optical device (e.g., of the light source 814 and/or light sensor 816). Additionally or alternatively, operating the optical device according to an operational mode could include operating actuators, servos, or other actuators (not shown) to control a configuration of elements of the optical device (e.g., to alter a configuration of optics (e.g., to change a focal length), to change the relative location and/or angle of the light source 814 relative to the light sensor 816 and/or optics of the optical device).

The detector 812 could be configured in a variety of ways to detect a variety of other properties of the intervening and/or target tissues. For example, the detector 812 could include an acoustical transducer, an optical coherence tomography (OCT) sensor, a visible light camera, an infrared camera, or some other components configured to detect a thickness of the intervening tissue, a depth of the target tissue beneath the external body surface (i.e., beneath the surface of a wrist of a wearer), or some other property of the location, thickness, and/or other properties of various elements and tissues of a wearer or other user. The detector 812 could be additionally or alternatively configured to detect a temperature, a scattering coefficient, an extinction coefficient, an absorbance spectrum, a water content and/or hydration level, a color, a melanin content, a fat content, or some other property or properties of the intervening tissue, the target tissue, and or some other tissues of a wearer and/or some other biological environment.

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, the detector 812, light source 814, and light sensor 816. For example, the controller 872 may operate light source 814, light sensor 816 and/or detector 812 during each of a set of pre-set measurement periods. In particular, the controller module 872 can include instructions for operating the light source 814 to emit illumination into a target tissue of a through an external body surface and intervening tissue between the target tissue and the external body surface and operating the light sensor 816 to detect one or more properties of light emitted by the target tissue through the intervening tissue and the external body surface. Such instructions could include instructions to perform such operations of the light source 814 and light sensor 816 and/or to configure the light source 814 and light sensor 816 according to an operational mode stored in the operational mode data 862. Such instructions could further include instructions to operate the detector 812 and/or the light source 814 and light sensor 816 to detect an other property of the target tissue and/or the intervening tissue and to select an operational mode from the operational mode data 862 based on the detected other property.

The controller module 872 can also include instructions for operating a user interface 820. For example, controller module 872 may include instructions for displaying data collected by the data collection system 810 and analyzed by the calculation and decision module 874, or for displaying one or more alerts generated by the alert module 875. Further, controller module 872 may include instructions to execute certain functions based on inputs accepted by the user interface 820, such as inputs accepted by one or more buttons disposed on the user interface.

Communication platform 830 may also be operated by instructions within the controller module 872, such as instructions for sending and/or receiving information via a wireless antenna, which may be disposed on or in the device 800. The communication interface 830 can optionally include one or more oscillators, mixers, frequency injectors, etc. to modulate and/or demodulate information on a carrier frequency to be transmitted and/or received by the antenna. In some examples, the device 800 is configured to indicate an output from the processor by modulating an impedance of the antenna in a manner that is perceivable by a remote server or other remote computing device.

Calculation and decision module 872 may include instructions for receiving data from the data collection system 810, analyzing the data to determine one or more physiological parameter(s) of the target tissue, such as concentration of a target analyte, analyzing the data to determine if a medical condition is indicated, or other analytical processes relating to the biological environment proximate to the device 800. These instructions could be executed at each of a set of preset measurement times. Further, calculation and decision module 872 could include instructions for creating, updating, or otherwise modifying the operational mode data 862 according to data generated by the data collection system 810 and/or the outcome of simulated operation of optical device (e.g., light source 814 and light sensor 816) to detect a target property of the target tissue. Additionally or alternatively, the operational mode data 862 could be preprogrammed in the device 800 and/or received from a server or other remote system (e.g., via the communication interface(s) 830) based on simulated operation of the optical device, statistical information about a population of wearers and/or users, experimental results, or some other process(es).

The program instructions of the calculation and decision module 872 may, in some examples, be stored in a computer-readable medium and executed by a processor located external to the device 800. For example, the device 800 could be configured to collect certain data regarding physiological parameters from the wearer and then transmit the data to a remote server, which may include a mobile device, a personal computer, the cloud, or any other remote system, for further processing.

The computer readable medium 860 may further contain other data or information, such as medical and health history of a wearer of the device 800, that may be useful in determining whether a medical condition is indicated. Further, the computer readable medium 860 may contain data corresponding to certain mean analyte levels, blood oxygen saturations, or other baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the wearer of the device 800 based on data collected over a certain number of measurement periods. For example, the calculation and decision module 874 may generate a baseline concentration of a target blood analyte for each of a plurality of measurement periods by averaging the analyte concentration at each of the measurement periods measured over the course of a few days, and store those baseline concentrations in the computer readable medium 860 for later comparison. Baselines may also be generated by a remote server and transmitted to the wearable device 800 via communication interface 830. The calculation and decision module 874 may also, upon determining that a medical condition is indicated, generate one or more recommendations for the wearer of the device 800 based, at least in part, on consultation of a clinical protocol. Such recommendations may alternatively be generated by the remote server and transmitted to the device 800.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical condition is indicated, the alert module 876 may generate an alert via the user interface 820. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

VI. Illustrative Methods

Figure 9:
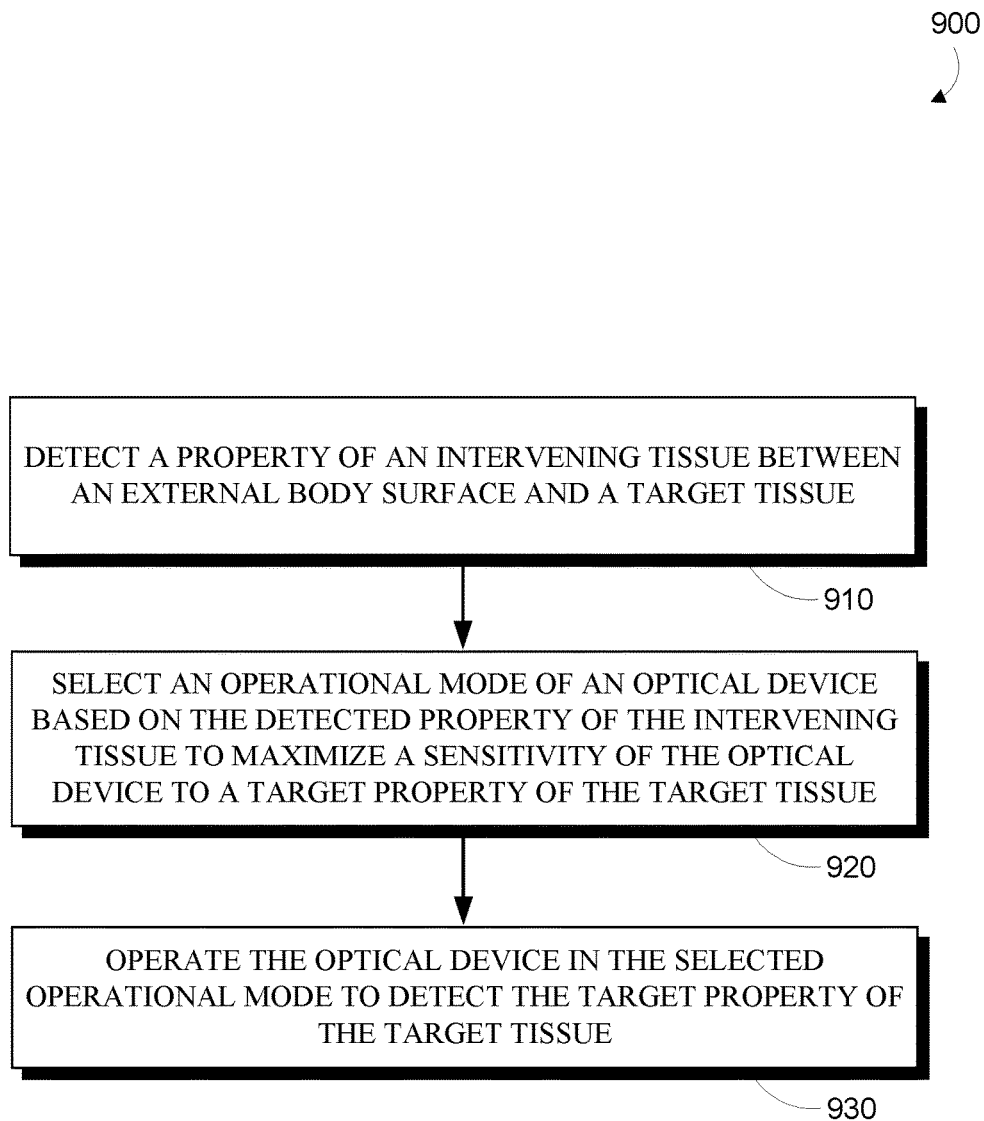
FIG. 9 is a flowchart of an example method.

FIG. 9 is a flowchart of a method 900 for using an optical device to detect a target property of a target tissue. The target tissue could be a portion of subsurface vasculature (e.g., an artery or vein near the skin of a wrist of a person), a tendon, a muscle, a nerve, or some other tissue of a body. Further, the target property could be an oxygen saturation of blood in the target tissue, the location, concentration, or other properties of fluorophores in the target tissue (e.g., fluorophores configured to selectively interact with an analyte of interest), or some other property or properties of the target tissue. The optical device is configured to illuminate the target tissue (e.g., by including an LED, laser, or other light-emitting elements and associated components, e.g., optics) through an external body surface and an intervening tissue (i.e., a tissue between the external body surface and the target tissue). The optical device is further configured to detect light emitted from the target tissue (e.g., by including a CCD, active pixel sensor, photodiode, or other light sensitive element(s) and/or arrays thereof) through the intervening tissue and the external body surface in response to the illumination.

The method 900 includes detecting a property of the intervening tissue between the external body surface and the target tissue (910). This can include operating components of the optical device that are used to illuminate and to detect light form the target tissue to detect the property of the intervening tissue (910). Additionally or alternatively, the optical device could include an additional detector (e.g., an acoustical detector, an optical coherence tomography detector, a color sensor, a further optical detector, or some other sensor or sensors) configured to detect the property of the intervening tissue (910). The property of the intervening tissue could include at least one of a thickness, a melanin content, an optical absorption, a scattering property, or some other independently measured property of the intervening tissue.

The method 900 additionally includes selecting an operational mode of the optical device based on the detected property of the intervening tissue to maximize a sensitivity of the optical device to the target property of the target tissue (920). This can include using calibration curves, look-up tables, or other methods to determine parameters of the configuration and/or operation of the optical device defined by an operational mode of the optical device. An operational mode can be defined, specified, calculated, or otherwise selected as described elsewhere herein. Further, operational modes and associated information (e.g., calibration curves, look-up tables, etc.) could be determined through simulation of the operation of the optical device to optically interrogate the target tissue (i.e., to optically detect the target property of the target tissue). Operational modes could be determined based on such simulations to maximize the sensitivity or some other figure of merit of the optical detector in detecting the target property.

The method 900 additionally includes operating the optical device in the selected operational mode to detect the target property of the target tissue (930). This can include operating a light source and associated elements of the optical device to produce illumination having a specified wavelength, spectral content, beam width, beam shape, wavefront, location, orientation, or other properties according to the selected operational mode. Operating the optical device in the selected operational mode (930) can include operating a light detector and associated elements of the optical device to detect light from the target tissue according to a specified field of view, wavelength sensitivity profile, focus, exposure time, sensor integration time, or other properties according to the selected operational mode. Operating the optical device in the selected operational mode (930) can include operating one or more servos, motors, or other actuators to configure elements of the optical device (e.g., the location and orientation of optics (e.g., lenses, mirrors, filters, diffraction gratings) of the optical device, the location and orientation of a light source and/or light sensor of the optical device relative to the target tissue and/or other elements of the optical device). Other aspects of operating the optical device in the selected operational mode (930) are anticipated.

The method 900 could include additional steps or elements in addition to detect the property of the intervening tissue (910), selecting an operational mode of the optical device based on the detected property (920), and operating the optical device in the selected operational mode to detect the target property of the target tissue (930). For example, the method 900 could include introducing a contrast agent (e.g., a fluorophore configured to selectively interact with an analyte of interest) to the target tissue (e.g., by injection of the contrast agent into a portion of subsurface vasculature). The method 900 could include updating operational modes and/or associated information (e.g., calibration curves) based on the operation of the device to detect the target property or according to some other operation of the optical device. The method 900 could include determining that a property of the detection of the target property by the optical device (e.g., a noise level, a noise distribution, a repeatability, an accuracy relative to some other sensor or information source, a spectral content) is above/below a specified threshold and responsively selecting a second operational mode of the optical device based on a second detected property of the intervening tissue. Other additional and/or alternative elements of method 1000 are anticipated.

VII. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A method comprising:
   detecting a thickness of an intervening tissue between an external body surface and a target tissue, wherein the target tissue comprises a portion of subsurface vasculature;
   selecting an operational mode of an optical device, wherein the optical device comprises a light source, a light sensor, and optics, and the selected operational mode is a specified configuration or operation of the light source, light sensor, and/or optics for detecting an optical property of the target tissue through the intervening tissue, wherein selecting the operational mode of the optical device comprises using a calibration curve or look-up table that relates the detected thickness of the intervening tissue to the specified configuration or operation of the light source, light sensor, and/or optics; and
   operating the optical device in the selected operational mode to detect an optical property of the target tissue, wherein operating the optical device to detect the optical property of the target tissue comprises emitting, by the light source, light through the external body surface and the intervening tissue to illuminate the target tissue according to the selected operational mode and detecting, by the light sensor, light emitted from the target tissue through the intervening tissue and the external body surface in response to the illumination according to the selected operational mode.

2. The method of claim 1, wherein the portion of subsurface vasculature comprises an artery or a vein.

3. The method of claim 1, wherein the optical property of the target tissue is related to an oxygen saturation of blood in the portion of subsurface vasculature.

4. The method of claim 1, wherein the optical property of the target tissue is related to a fluorophore in the portion of subsurface vasculature.

5. The method of claim 1, wherein detecting the thickness of the intervening tissue comprises operating the optical device to illuminate the intervening tissue through the external body surface, detecting light received from the intervening tissue through the external body surface in response to the illumination, and determining the thickness of the intervening tissue based on the detected light.

6. The method of claim 1, wherein emitting light through the external body surface and the intervening tissue to illuminate the target tissue according to the selected operational mode of the optical device comprises emitting a beam of illumination having a beam diameter specified by the selected operational mode.

7. The method of claim 1, wherein detecting light emitted from the target tissue through the intervening tissue and the external body surface in response to the illumination according to the selected operational mode comprises detecting light received from the target tissue through the intervening tissue and the external body surface within a specified field of view, wherein the specified field of view is specified by the selected operational mode.

8. The method of claim 7, wherein the light sensor comprises a multipixel photodetector, wherein detecting light received from the target tissue through the intervening tissue and the external body surface within a specified field of view comprises detecting light received from the target tissue through the intervening tissue and the external body surface by a specified set of pixels of the multipixel photodetector.

9. The method of claim 1, wherein the calibration curve or look-up table is developed based on simulated operation of the optical device to detect an optical property of a simulated target tissue through a simulated external body surface and simulated intervening tissue.

10. A device comprising:
    a light source for illuminating a target tissue through an external body surface and an intervening tissue between the external body surface and the target tissue, wherein the target tissue comprises a portion of subsurface vasculature;
    a light sensor for detecting light emitted from the target tissue through the intervening tissue and the external body surface in response to illumination by the light source;
    optics coupled to the light source and light sensor; and
    a controller, wherein the controller is programmed to:
    detect a thickness of the intervening tissue;
    select an operational mode of the device, wherein the selected operational mode is a specified configuration or operation of the light source, light sensor, and/or optics for detecting an optical property of the target tissue through the intervening tissue, wherein selecting the operational mode of the device comprises using a calibration curve or look-up table that relates the detected thickness of the intervening tissue to the specified configuration or operation of the light source, light sensor, and/or optics; and
    operate the device in the selected operational mode to detect an optical property of the target tissue, wherein operating the device to detect the optical property of the target tissue comprises operating the light source to emit light through the external body surface and the intervening tissue to illuminate the target tissue according to the selected operational mode and operating the light sensor to detect light emitted from the target tissue through the intervening tissue and the external body surface in response to the illumination according to the selected operational mode.

11. The device of claim 10, further comprising a detector configured to detect the thickness of the intervening tissue.

12. The device of claim 11, wherein the detector is configured to detect the thickness of the intervening tissue using optical coherence tomography (OCT).

13. The device of claim 11, wherein the detector is configured to detect the thickness of the intervening tissue acoustically.

14. The device of claim 10, further comprising a mount configured to mount the light source and the light sensor to the external body surface.

15. The device of claim 10, wherein the light sensor comprises a multipixel photodetector.

16. The device of claim 10, wherein the light source comprises a coherent light source.

17. The device of claim 10, wherein the light source emits a beam of illumination, and wherein the light source comprises a beam shaper that controls a beam diameter of the emitted beam of illumination.

18. The device of claim 10, wherein operating the light source to emit light through the external body surface and the intervening tissue to illuminate the target tissue according to the selected operational mode comprises emitting a beam of illumination having a beam diameter specified by the selected operational mode.

19. The device of claim 10, wherein operating the light sensor to detect light emitted from the target tissue through the intervening tissue and the external body surface in response to the illumination according to the selected operational mode comprises detecting light received from the target tissue through the intervening tissue and the external body surface within a specified field of view, wherein the specified field of view is specified by the selected operational mode.

20. The device of claim 10, wherein the calibration curve or look-up table is developed based on simulation operation of the device to detect an optical property of a simulated target tissue through a simulated external body surface and simulated intervening tissue.

\* \* \* \* \*